United States Patent [19]

Rodwell et al.

[11] Patent Number: 5,196,510

[45] Date of Patent: Mar. 23, 1993

[54] MOLECULAR RECOGNITION UNITS

[75] Inventors: John D. Rodwell, Yardley; Thomas J. McKearn, New Hope; Vernon L. Alvarez, Morrisville, all of Pa.; Robert D. Radcliffe, Titusville, N.J.

[73] Assignee: Cytogen Corporation, Princeton, N.J.

[21] Appl. No.: 519,702

[22] Filed: May 7, 1990

Related U.S. Application Data

[63] Continuation-in-part of Ser. No. 291,730, Dec. 29, 1988, abandoned.

[51] Int. Cl.$^5$ .................... C07K 7/08; C07K 7/10; A61K 43/00; G01N 33/533
[52] U.S. Cl. .................... 530/324; 530/326; 424/1.1; 424/2; 436/545; 436/546
[58] Field of Search .................. 436/513, 545, 546; 530/324, 326; 424/2

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,629,783 | 12/1986 | Cosand | 530/324 |
| 4,683,291 | 7/1987 | Zimmerman et al. | 530/324 |
| 4,741,900 | 5/1988 | Alvarez et al. | 424/85 |
| 4,792,525 | 12/1988 | Rusolahti et al. | 435/240.23 |
| 4,879,237 | 11/1989 | Ruoslahti et al. | 435/240.2 |

FOREIGN PATENT DOCUMENTS

| | | |
|---|---|---|
| 0368684 | 5/1990 | European Pat. Off. |
| 88/09344 | 12/1988 | PCT Int'l Appl. |
| 89/05150 | 6/1989 | PCT Int'l Appl. |

OTHER PUBLICATIONS

Neuberger et al., "Recombinant Antibodies Possessing Novel Effector Functions," Nature 312:604–608 (1984).
Journal of Biological Chemistry, 260, Oct. 1985, Gartner et al., pp. 11891–11894.
Proceedings National Academy Sciences USA, 76, Jan. 1979, Yoshida et al., pp. 486–490.
EMBO Journal, 6, Oct. 1987, Altaba et al., pp. 3065–3070.
Cell, 37, May 1984, Richards et al., pp. 263–272.
Bioessays, 8, No. 2, Feb./Mar. 1988, Verhoeyen et al., pp. 74–78.
Science, 239 Jan. 1988, Saiki et al., pp. 487–491.
Mazza et al., 1985, Ann. Inst. Pasteur. Immunol. 136D:259–269.
Williams et al., 1988, Proc. Nat'l Acad. Scil 85: 6488–92.
Goni et al., 1988, J. Immunol 135: 4073–79.
Taub et al., 1989, J. Biol. Chem. 264: 259–65.
Williams et al., 1989, Biotech. 7: 471–574.
Rodwell et al., 1989, Nature 342: 99–100.

*Primary Examiner*—Christine M. Nucker
*Assistant Examiner*—M. P. Woodward
*Attorney, Agent, or Firm*—Pennie & Edmonds

[57] ABSTRACT

A system or method for identifying and/or designing novel peptides and polypeptides comprising an amino acid sequence which mimics the molecular recognition site of either (a) a macromolecule such as an immunoglobulin, an enzyme, a receptor protein, a lectin or other binding protein or (b) a small molecule or a small region of a large molecule which functions as a ligand and is recognized and binds specifically to a macromolecule is disclosed. Novel peptides and polypeptides as well as conjugates of the peptides and polypeptides are also disclosed. Applications for use of the peptides, polypeptides and conjugates in a wide range of fields such as biomedicine; biological control and pest regulation; agriculture; cosmetics; environmental control and waste management; chemistry; catalysis; nutrition and food industries; military uses; climate control, etc. are disclosed.

16 Claims, 9 Drawing Sheets

8 MIN.
FIG. 3A(ii) 
10 MIN.
FIG. 3A(iii) 
3.5 HR

IMMED.
FIG. 3B(ii) 
5 MIN.
FIG. 3B(iii) 
3.5 HR
FIG. 3B(iv) 
4 HR
POST
THROMBUS
REMOVAL FIG. 3C(i)
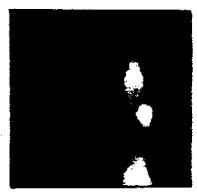
178m
FIG. 3C(ii)
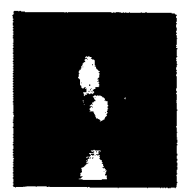
187m
FIG. 3C(iii)
197m
FIG. 3C(iv)
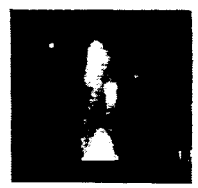
212m
FIG. 3C(v)
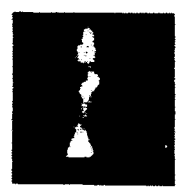
225m
FIG. 3C(vi)
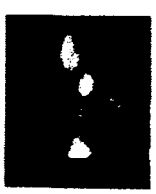
POST THROMBUS REMOVAL FIG. 3D(i)
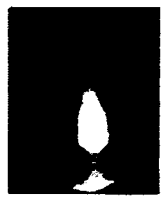
6 MIN
FIG. 3D(ii)
16 MIN
FIG. 3D(iii)
26 MIN
FIG. 3D(iv)
36 MIN
FIG. 3D(v)
134 MIN
FIG. 3D(vi)
144 MIN
FIG. 3D(vii)
180 MIN
FIG. 3D(viii)
4 HR

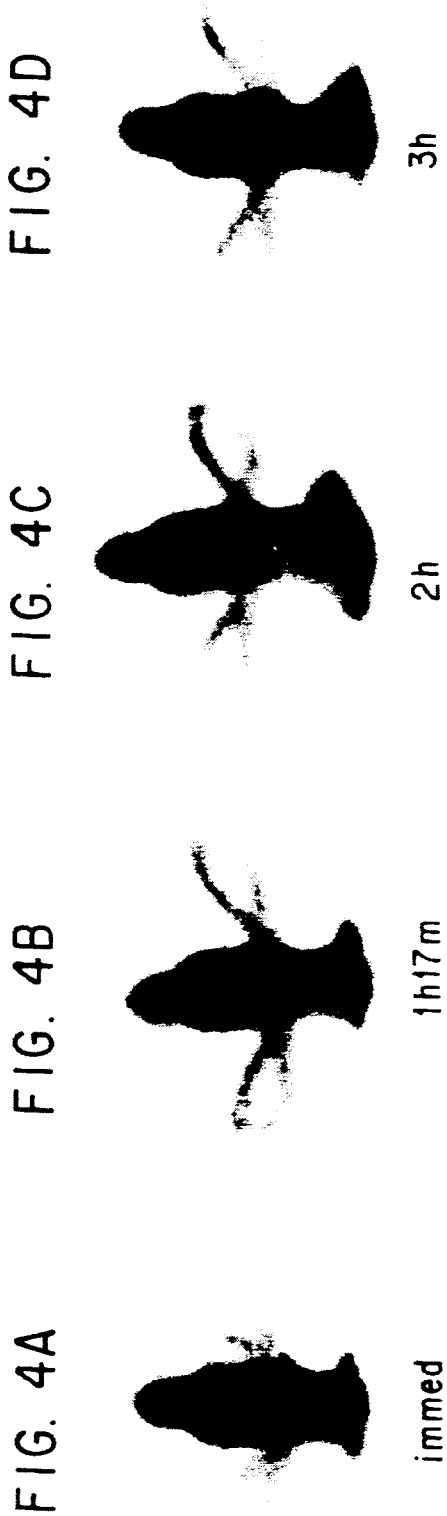

1 hr 2 hr 3 hr 4 hr 12 m 1 hr 3 hr 4 hr

MOLECULAR RECOGNITION UNITS

CROSS-REFERENCE TO RELATED APPLICATION

This is a continuation in part of application Ser. No. 07/291,730 filed on Dec. 29, 1988 now abandoned, the disclosure of which is incorporated herein by reference.

TABLE OF CONTENTS

1. Field of the Invention
2. Background of the Invention
3. Summary of the Invention
4. Definitions
5. Brief Description of the Figures
6. Detailed Description of the Invention
   6.1. Method for Identifying and/or Designing MRUs
      6.1.1. Immunoselecting B Cells
      6.1.2. Screening for Early B Cells
      6.1.3. Determining the Sequence of the Rearranged CDR
         6.1.3.1. Nucleotide Sequences
      6.1.4. Synthesizing MRUs
   6.2. MRUs With Enhanced Affinity
   6.3. Ags
   6.4. Conjugates
   6.5. Applications for MRUs and Conjugates of MRUs
7. Example: Preparation of an MRU
8. Example: A Family of Conjugates Useful for Imaging Thrombi
   8.1. Conjugates of MRUs: Anti-Thrombic Fusion Peptides
   8.2. Activity of Fusion Peptides
      8.2.1. Plasma Stability of Fusion Peptides
      8.2.2. Inhibition of Platelet Aggregation and Binding of Platelets to PAC-1 Antibody
   8.3. Use of Fusion Peptides for In Vivo Imaging

1. FIELD OF THE INVENTION

The present invention relates to a system or method for identifying and/or designing peptides and polypeptides which mimic the binding specificity of a number of naturally occurring macromolecules which recognize and bind specifically to small molecules or small regions of large molecules. The invention further relates to a method for designing peptides and polypeptides which mimic the molecular topography of small molecules or small regions of large molecules which function as ligands and are recognized by and bind specifically to the naturally occurring macromolecules.

More particularly, the invention encompasses a method for identifying and/or designing novel peptides and polypeptides which comprise an amino acid sequence which mimics the molecular recognition site, and hence the binding specificity, of macromolecules including, but not limited to: immunoglobulins or antibodies, enzymes, receptor proteins, lectins and other binding proteins such as avidin and streptavidin, etc. Additionally, the invention encompasses a method for designing novel peptides and polypeptides which comprise an amino acid sequence which mimics the molecular recognition site of small molecules or small regions of large molecules which function as ligands and are recognized by and bind specifically to a wide range of naturally occurring macromolecules. Examples of molecules which function as ligands include, but are not limited to antigens; hormones, pheromones, neurotransmitters, signal proteins and peptides, prostaglandins, etc.

The invention further encompasses the novel peptides and polypeptides prepared according to the method or system described herein. Also encompassed are novel conjugates in which a peptide or polypeptide of the invention is attached, either directly or via a linker moiety, to a second compound. The conjugates, include, but are not limited to fusion proteins and peptides containing the novel peptides and polypeptides.

In addition, the invention encompasses the nucleotide sequences which encode the novel peptides and polypeptides prepared by the method described.

The novel peptides, polypeptides and conjugates of the invention are advantageously used for a wide range of applications including uses in the fields of biomedicine; biological control and pest regulation; agriculture; cosmetics; environmental control and waste management; chemistry; catalysis; nutrition and food industries; military uses; and climate control.

2. BACKGROUND OF THE INVENTION

Molecular recognition, i.e. the ability to specifically recognize and bind another molecule such as a ligand or a substrate is an important functional property of a number of naturally occurring macromolecules which are critically important to biological and/or biochemical systems. Formation of the macromolecule/ligand complex leads to additional processes depending upon the nature of the particular macromolecule and, at times, upon the environment in which the complex forms. For instance, recognition and binding of an enzyme to its substrate leads to chemical changes in that substrate; recognition and binding of an antibody or immunoglobulin to its antigen, to immobilization and/or inactivation of such antigen; recognition and binding of a carrier or transport protein to its ligand, to transport of the ligand from one site to another; recognition and binding of a hormone receptor to its hormone, to changes in cellular activity; recognition and binding of a contractile protein to its ligand, to mechanical work; etc. Thus, these naturally occurring macromolecules and their ligands are a critical component of living systems and are particularly useful in biology and medicine for delivery of agents to target sites, for diagnosis, therapy, bioregulation, separations and preparations etc. In addition, macromolecules and their ligands find uses in numerous non-medical, non-biological, industrial applications such as separations, preparations, catalysis and monitoring of chemicals and other substances.

Efficient and inexpensive methods for preparing homogenous macromolecules and/or ligands for such macromolecules in large quantities are highly desired. The development of monoclonal antibody techniques has provided a fairly efficient means to obtain homogenous supplies of one category of macromolecules, i.e. antibodies or immunoglobulins. Recombinant DNA technology has also provided the means to obtain homogenous supplies of some proteinaceous macromolecules and ligands. Chemical synthetic methods can provide a means for preparing some macromolecules and ligands, provided knowledge of the structure and chemical composition of such substances is available.

Despite the above mentioned techniques, there still exists a very real need for efficient, inexpensive methods for preparing large, homogeneous amounts of macromolecules and their ligands, whether proteinaceous or not, for biomedical and industrial applications. Moreover, in certain instances, it is desired to prepare substances having the molecular recognition and binding specificity of a naturally occurring macromolecule without additional effector activity of such molecule. To illustrate, it may be desired to obtain a molecule having the specific binding activity of a given antibody without the additional activity of such antibody such as complement-mediated cell lysis or hypersensitive or allergic reactions mediated by binding of the Fc region of the antibody to cell surface receptors. Thus, there exists a need for an efficient method to prepare molecules that can mimic the binding specificity of either a naturally occurring macromolecule or a ligand which is recognized by the naturally occurring macromolecule.

A method for preparing large, single polypeptide chains which are stated to have the characteristics and binding specificity of the antigen binding region of antibodies is described by Ladner (International Pat. Application No. PCT/US87/02208 published on Mar. 10, 1988; see also U.S. Pat. No. 4704692 issued on Nov. 3, 1987). According to this method, one or more peptide linkers are devised using a computer-based system and are used to join the variable regions of an antibody to form a single polypeptide chain of approximately 215-250 amino acid residues which exhibits three-dimensional topography similar to that of the original antibody. The nucleotide sequence encoding such large polypeptide is deduced, synthesized and inserted using recombinant DNA techniques into a suitable host cell which expresses the desired polypeptide.

Unlike the method described by Ladner which provides large polypeptide molecules of about 215-250 amino acid residues, the presently claimed method provides small peptides and polypeptides of less than about 40-45 amino acid residues which mimic the binding specificity of macromolecules and ligands. In addition, the present method does not require the preparation and synthesis of linkers which are necessary according to Ladner to enable the large polypeptide chains to mimic the binding of an antibody molecule. Moreover, although recombinant DNA techniques can be employed to prepare the presently claimed peptides, polypeptides and conjugates, unlike the method of Ladner, the present method does not require such techniques. Less expensive, efficient chemical synthetic methods can advantageously be used to prepare the presently claimed compositions.

Bruck et al. (1986, Proc. Nat'l Acad. Sci. USA 83:6578-82) describes the molecular cloning and nucleic acid sequence of the heavy and light variable regions and ($V_H$ and $V_L$) of an anti-idiotypic monoclonal antibody, 87.92.6, which is stated to antigenically and functionally mimic the receptor binding structure of the retrovirus type 3 hemagglutinin (HA). Bruck et al. state that their results suggest that molecular mimicry of the viral HA glycoprotein by the anti-idiotypic antibody may be created by a stretch of homologous amino acids on the antibody $V_L$. The authors conclude that proteinaceous antigen mimicry by antibodies is achieved by sharing primary structure, i.e. homologous amino acid sequences found on the antigen and antibody.

Unlike the disclosure of Bruck et al., the method of the present invention allows the generation of small peptides and polypeptides having the binding specificity of a macromolecule or a ligand in the absence of knowledge of the primary structure of the macromolecule or ligand intended to be mimicked. Moreover, the present method can be employed to prepare peptides and polypeptides which mimic the binding activity of non-peptide ligands as well as peptide or proteinaceous ligands.

3. SUMMARY OF THE INVENTION

The present invention encompasses a novel and efficient method or system for identifying and/or designing novel peptides and polypeptides comprising an amino acid sequence which mimics a molecular recognition site and hence the binding specificity of a naturally occurring macromolecule or of a small molecule or small region of a large molecule which functions as a ligand for a naturally occurring macromolecule. The invention also encompasses the novel peptides and polypeptides designed according to the method or system as well as conjugates containing these peptides and polypeptides. Additionally, the invention encompasses the nucleotide sequences encoding the novel peptides and polypeptides designed according to the method or system described.

The method of the invention for identifying and/or designing and preparing a novel molecular recognition units comprises:

(1) immunoselecting B cells which express an IgM immunoglobulin which binds specifically to a molecule which is or contains a molecular recognition site which is complementary to that of the molecular recognition unit desired;

(2) screening the selected B cells from step (1) to identify early B cells, i.e., those in which the sequence of deoxyribonucleotides expressed has been rearranged in only one complementarity determining region when compared to that of germline genes;

(3) determining the nucleotide sequence of or the amino acid sequence encoded by the rearranged complementarity determining region identified in step (2); and (4) synthesizing the desired molecular recognition unit encoded by the sequence identified in step (3) above.

According to one embodiment, B cell lymphocytes are immunoselected by (a) stimulating the production of B cell lymphocytes which are specific for an antigen or a hapten which is or contains a molecular recognition site complementary to the site desired to be mimicked; (b) immortalizing the stimulated B cell lymphocytes; and (c) screening the immortalized cells to identify B cells which secrete the desired IgM immunoglobulin which binds specifically to a molecule which is or contains a molecular recognition site complementary to that of the desired molecular recognition unit.

According to another alternative embodiment, B cell lymphocytes are "immunoselected" by screening the publicly known and/or available immortalized cell lines which produce monoclonal antibodies of the IgM isotype to identify those which react specifically with an antigen or a hapten which is or contains a molecular recognition site complementary to the desired molecular recognition unit.

The method of the invention is particularly advantageous because it can be employed to design novel peptides and polypeptides of less than about 40-45 amino acid residues that mimic the binding specificity of a very large number of molecules which contain a molecular recognition site. Indeed, the method can be employed to mimic the binding specificty of any molecule containing a molecular recognition site so long as the molecule can function as a hapten or an antigen. Thus, the molecules which can be mimicked by a peptide or polypeptide of the invention need not be peptides or polypeptides. Moreover, knowledge of the primary structure or sequence of the molecule whose binding specificity is desired to be mimicked is not required for the present method.

In addition, the method of the invention is advantageous because it provides a homogeneous supply of low molecular weight peptides and polypeptides that possess the ability to recognize and specifically bind to a desired molecular recognition site. When intended for particular in vivo uses, the peptides and polypeptides can be designed to have lower immunogenicity. On the other hand, when intended for other in vivo uses, such as for vaccines, the peptides and polypeptides can be designed to have enhanced immunogenicity.

Finally, the invention provides methods for using the novel peptides, polypeptides and conjugates for a myriad of applications in a wide range of fields including biomedicine; biological control and pest regulation; agriculture; cosmetics; environmental control and waste management; chemistry; catalysis; nutrition and food industries; military uses; and climate control.

4. DEFINITIONS

As used throughout the present specification, the term "Molecular Recognition Unit" (hereinafter "MRU") is intended to encompass a peptide or polypeptide which comprises an amino acid sequence that mimics a molecular recognition site.

The term "molecular recognition site" is intended to encompass a domain or region of a macromolecule which recognizes and binds specifically to a small molecule or a small region of a large molecule. Examples of such molecular recognition sites include, but are not limited to: an antigen-binding site formed by hypervariable regions, also known as complementarity-determining regions ("CDRs"), of the heavy and light chains of immunoglobulins; a ligand binding site of an enzyme such as a substrate or a cofactor binding site; a ligand binding site of a receptor protein or other binding protein, etc. The term "molecular recognition site" is further intended to encompass a small molecule or a small domain of a molecule which functions as a ligand that binds specifically to a naturally occurring macromolecule. Examples of such ligands include, but are not limited to: hormones; pheromones; signal substances such as neurotransmitters, signal proteins and peptides, etc; enzyme substrates and cofactors; ligands for receptor proteins; antigens; etc.

The term "ligand" is intended to encompass a substance that specifically binds to or "fits" a molecular recognition site on a macromolecule.

The term "mimics" is intended to mean resembles closely or simulates.

The term "early B cells" is intended to encompass B cell lymphocytes or immortalized cell lines derived from B cell lymphocytes in which the genetic information encoded in the sequence of deoxyribonucleotides expressed has been rearranged in only one complementarity determining region ("CDR") when compared to that of germline genes. As used herein, the term "rearrangement" of the sequence of deoxyribonucleotides is intended to encompass one or more of a variety of alterations including mutation, recombination, insertion and/or deletion of a nucleotide(s) from the original germline sequence of the variable region gene(s).

Throughout the present specification, the one-letter symbols are used to indicate amino acids as follows: Alanine, A; Arginine, R; Asparagine, N; Aspartic acid, D; Asparagine or aspartic acid, B; Cysteine or cystine, C; Glutamine, Q; Glutamic acid, E; Glutamine or glutamic acid, Z; Glycine, G; Histidine, H; Isoleucine, I; Leucine, L; Lysine, K; Methionine, M; Phenylalanine, F; Proline, P; Serine, S; Thr T; Tryptophan, W; Tyrosine, Y; Valine, V.

5. BRIEF DESCRIPTION OF THE FIGURES

The present invention can be more fully understood by reference to the following Detailed Description, Examples and appended Figures in which:

FIG. 1 graphically represents the stability in plasma of representative Tc-99m labeled fusion peptides of the invention.

FIG. 2 is a graphic illustration of the clearance from blood of a Tc-99m labeled peptide, designated "Pac-2" which is a fusion peptide of the sequence: ARR-SPYYRGDGAGPYYAMDYDKCTCCA, after administration to an experimental animal (rabbit). The clearance of I-125 labeled fibrinogen is also illustrated for comparison.

FIG. 3 (A-D) illustrates representative gamma camera images obtained with purified fusion peptides in rabbits with thrombi induced in the left jugular vein. FIG. 3 (A(i-iii) and B(i-iv)) exemplifies 2 rabbits imaged after injection of a Tc-99m labeled irrelevant fusion peptide, designated Pac-3 (negative control). FIG. 3 (C(i-vi) and D(i-viii)) exemplifies 2 rabbits imaged after injection of Tc-99m labeled fusion peptide of the sequence: ac-SYGRGDVRGDFKCTCCA-a (see text Section 8.3 for details).

FIG. 4 (A-E) illustrates representative gamma camera images obtained from a rabbit with a thrombus induced in the left jugular vein after injection of a Tc-99m labeled fusion peptide, designated "Pac-16," of the sequence: ac-PSYYRGDGAPSYYRGDGAPSYYRG-DAKCTCCA-a. Images were taken immediately, 1 hour 17 min., 2, 3 and 4 hours after injection of the fusion peptide (see text Section 8.3 for details).

6. DETAILED DESCRIPTION OF THE

Figure 1:
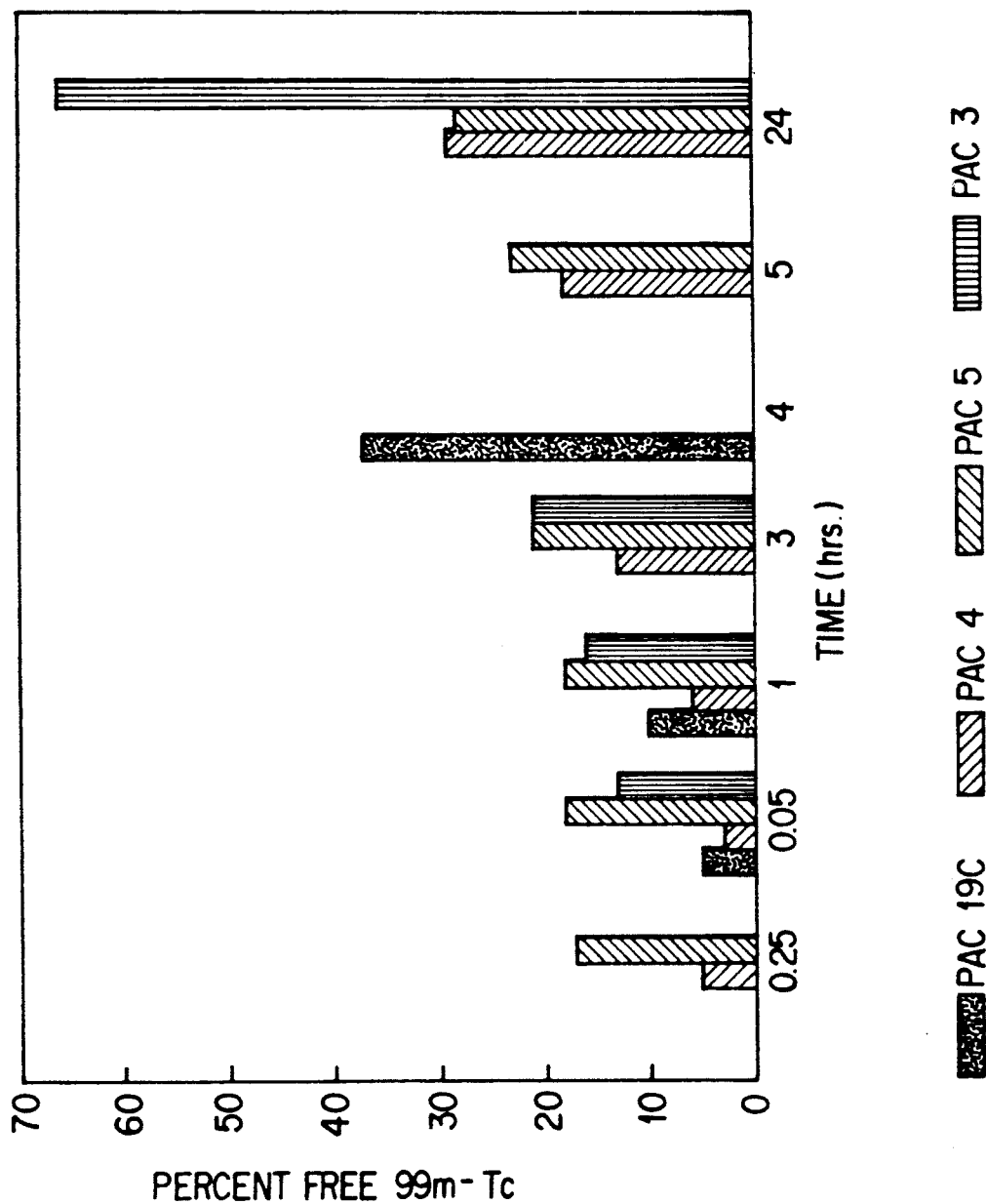

The present invention provides a system or method for identifying and/or designing novel peptides and polypeptides termed "Molecular Recognition Units" (hereinafter "MRUs") which comprise an amino acid sequence which mimics a molecular recognition site. The molecular recognition site may be found either (a) on a naturally occurring macromolecule which binds specifically a small molecule or a small region of another macromolecule or (b) on a ligand which binds specifically to a naturally occurring macromolecule.

Thus, the MRUs of the present invention mimic the binding specificity of a wide range of substances including a variety of naturally occurring macromolecules which include, but are not limited to: immunoglobulins; enzymes; receptor proteins; sensory receptors such as for taste, smell, etc.; deoxyribonucleic acid; ribonucleic acid; contractile proteins; lectins and other binding proteins such as avidin and streptavidin; etc. and a variety of ligands which include, but are not limited to: antigens; enzyme cofactors and substrates; enzyme activators and inhibitors; hormones; prostaglandins, neurohormones, growth factors; pheromones; signal substances such as neurotransmitters, signal proteins and peptides; biotin; pharmaceutical agents that bind to receptors or receptor proteins; transition state analogs for enzymes; etc.

Because the system of the invention entails an immunoselective method, it can advantageously be employed to design novel MRUs that mimic the binding specificity of a molecule so long as the molecule can function as a hapten or an antigen. Moreover, the system of the invention is particularly advantageous because it provides a means for rapidly designing and preparing novel peptides and polypeptides of minimum size, i.e., less than about 40–45 amino acid residues that can mimic the binding specificity of a wide variety of substances.

6.1. Method for Identifying and/or Designing MRUs

According to the present invention, the method for designing MRUs comprises the following four steps:

(1) immunoselecting B cells which express an IgM immunoglobulin which binds specifically to a molecule which is or contains a molecular recognition site which is complementary to that of the MRU desired;

(2) screening the selected B cells from step (1) to identify early B cells, i.e., those in which the sequence of deoxyribonucleotides expressed has been rearranged in only one CDR when compared to that of germline genes;

(3) determining the nucleotide sequence of or the amino acid sequence encoded by the rearranged CDR identified in step (2); and (4) synthesizing the desired MRU encoded by the sequence identified in step (3) above.

Each of these four steps is explained in detail below.

6 1.1. Immunoselecting B Cells

The immunoselection step provides a means for screening the repertoire of B cell lymphocytes to identify those that produce an IgM immunoglobulin which contains a molecular recognition site whose binding specificity will be mimicked by the desired MRU being prepared. It should be noted that when the desired MRU is intended to mimic a molecular recognition site of a macromolecule, the "antigen" employed in the immunoselection step is a ligand for the macromolecule. For example, to design an MRU which mimics the binding specificity of a hormone receptor, the hormone is employed as the "antigen" to immunoselect B cells. On the other hand, when the desired MRU is intended to mimic a molecular recognition site on a ligand, the "antigen" employed in the immunoselection step is a receptor or binding protein for the ligand. For example, to design an MRU which mimics the binding specification of a hormone, the hormone receptor or an anti-hormone antibody is employed as the "antigen" to immunoselect B cells. Hereinafter, the term "Ag" is used to encompass any molecule or substance containing a molecular recognition site which is employed as an "antigen" in the immunoselection step of the present method to induce an antibody response and thus includes molecules which function as ligands and molecules which function as receptors for ligands, including but not limited to antibodies (see infra, Section 6.3.).

Any means known in the art for immunoselecting B cell lymphocytes which express an IgM immunoglobulin which binds specifically to the Ag and thus contain a molecular recognition site whose binding specificity is desired to be mimicked is useful for this step of the present method.

According to one embodiment, B cell lymphocytes are immunoselected by (a) stimulating the production of B cell lymphocytes which are specific for an Ag which is or contains a molecular recognition site complementary to the site desired to be mimicked; (b) immortalizing the stimulated B cell lymphocytes; and (c) screening the immortalized cells to identify cells which secrete the desired IgM immunoglobulin which binds specifically to a molecule which is or contains a molecular recognition site complementary to that of the desired MRU.

In an in vivo process, B cell lymphocytes are stimulated by administering the Ag, alone or in combination with an adjuvant, to an animal and the desired B cells from the spleen, lymph nodes or peripheral blood of the immunized animal are collected.

The production of an enriched population of B cells which express immunoglobulin of the IgM isotype can be enhanced using an immunization schedule in which small doses of Ag are administered for only 2-3 days or in which a single large dose of Ag is administered at 3-4 days before collection of B cells. The amount of Ag required for the in vivo immunoselection of B cells depends upon the kind of animal used and the nature of the Ag and may readily be determined by one of ordinary skill. For example, when the animal employed is a mouse or a rat, then from about 1 to about 10 μg of carbohydrate Ag; from about 10 to about 50 μg of protein Ag; about 1 μg of a bacterial or viral Ag, and larger amounts of impure Ag generally not exceeding 1000 μg is used. Additionally, if the Ag is of low molecular weight, i.e., less than about 1000 daltons, or is poorly immunogenic for any other reason, it may first be coupled to a carrier prior to administration. Suitable carriers include keyhole limpet hemocyanin, bovine serum albumin, ovalbumin, fowl immunoglobulin or any other carrier known to those of skill in the art. The in vivo process for stimulating B cells is not limited to rodent species; other species are also advantageously used as a source of B cell lymphocytes.

Alternatively, B cell lymphocytes are stimulated by an in vitro "immunization" process. This in vitro process may be particularly advantageous when the Ag of choice is in limited supply because this process may be performed using nanogram amounts of Ag rather than the microgram amounts usually used for an in vivo immunization process. Moreover, the in vitro process is useful when the Ag is labile because it requires only a few days to complete. Finally, the in vitro process is useful when the Ag is particularly toxic in vivo or cannot be administered, for example to a human, for ethical considerations.

B cell lymphocytes are stimulated in vitro by culturing spleen cells, lymph node cells, tonsillar lymphocytes or peripheral blood lymphocytes in cell culture medium with the Ag of choice for a period of about 3-5 days.

When the cultured cells are obtained from a non-human animal species, it is advantageous to use thymocyte-conditioned cell culture medium. When the cultured cells are obtained for human volunteers, thymocyte-conditioned medium is not generally possible, but lymphokines may be used to stimulate proliferation of desired B cells. Additionally, in some instances, polyclonal activators of B cells such as bacterial lipopolysaccharide or mitogens such as pokeweed mitogen, phytohemagglutinin or conanavalin A can be included in the culture medium.

The B cell lymphocytes stimulated by any of the above described methods can be immortalized using any of a variety of methods known to those skilled in the art. For example, the fusion or hybridoma methods originally developed by Kohler and Milstein (reviewed by them in 1980, Sci. Amer. 243:66-74), the EBV transformation methods described by Kozbor et al. (1983, Immunol. Today 4:72-79), the EBV-hybridoma methods described by Cole et al. [in Monoclonal Antibodies and Cancer Therapy, Alan R. Liss, Inc., pp.77-96 (1985)] can be utilized to immortalize the selected B cells.

Once immortalized, the cells can be proliferated either in in vitro cell cultures or in vivo preferably as an ascites tumor or as a solid subcutaneous tumor in a compatible host animal. Alternatively, the immortalized cells can be stored frozen, for example, under liquid nitrogen and recloned periodically either in vitro or in vivo.

Generally when murine spleen cells are used, about $10^2$-$10^3$ cells are obtained at this stage of the first immunoselection step of the present method.

In order to identify B cells which secrete the desired IgM immunoglobulin, the immortalized hybridoma cells or transformed cells are cultured in vitro using cell culture medium for several days to a week or so. The supernatant is separated from the cells and tested for specificity and affinity for Ag. Any known screening technique, such as an enzyme-linked immunosorbent assay (ELISA), an immunofluorescent assay, e.g., using a fluorescence activated cell sorter (FACS), a radioimmunoassay, etc., in which the Ag is employed as the antigen is used to select B or hybridoma cells which express immunoglobulin of the desired specificity. The B or hybridoma cells must also be screened to identify those which express immunoglobulin of the IgM class. Any technique known to those of skill in the art, such as an ELISA, a radioimmunoassay, an indirect immunofluorescence assay, SDS-PAGE analysis of antibody labeled in vivo, an Ouchterlony assay, etc., can be used to determine the class of immunoglobulin produced [See, Goding, Monclonal Antibodies: Principles and Practice, 2d ed., Academic Press Inc., London 105-07 (1986); Campell, Laboratory Techniques in Biochemistry and Molecular Biology Vol. 13, Elsevier, Amsterdam, 187-93 (1984)]. Generally when murine spleen cells are used, this will represent about 10-30% of the immortalized B cells and thus about 100-300 such cells may be obtained in the first step of the invention.

According to another alternative embodiment, B cell lymphocytes can be "immunoselected" by screening the publicly known and/or available immortalized cell lines which produce monoclonal antibodies of the IgM isotype to identify those which react specifically with an Ag which is or contains a molecular recognition site complementary to the desired MRU. Such immortalized cell lines include hybridoma cell lines, EBV-transformed B lymphocyte cell lines, and cell lines formed by fusion of EBV-transformed B cells with myeloma or plasmacytoma cells. Such screening can be accomplished by computer searches of databases of published literature references and patents or by scanning the catalogues of monoclonal antibody producing cells deposited in and available from national depositories such as the American Type Culture Collection, Rockville, Md.; the Agricultural Research Culture Collection (NRRL), Peoria, Ill.; the Collection Nationale de l'Institut Pasteur de Cultures de Microorganisms, Paris, France; to name just a few.

6.1.2. Screening for Early B Cells

After a population of immortalized B cell lymphocytes which express IgM immunoglobulin specific for Ag of choice have been identified, the population is further screened to identify those in which the sequence of expressed deoxyribonucleotides that encode the IgM immunoglobulin has been rearranged in only a single CDR when compared to the germline sequence of deoxyribonucleotides, i.e., to identify early B cells.

According to this second step of the method of the invention, the total RNA is isolated or extracted from the immortalized B cells selected in step (1) using any technique known to those of skill in the art such as that described by Chirgwin et al. (1979, Biochem. 18:5294-99). The mRNA is separated from the rest of the RNA by affinity chromatography using either poly-U or poly-T bound to the column as described by Aviv et al. (1972, Proc. Nat'l Acad. Sci. 69:1408-13).

According to one embodiment of this step, the mRNA isolated from the selected B cells is dot blotted onto nitrocellulose filters which are then blocked to prevent subsequent non-specific binding of the labeled probe(s). Single stranded DNA oligonucleotide sequences corresponding to germline CDRs of the variable region genes from the animal from which the B cells were obtained are labeled using any known technique, including, but not limited to end labeling, nick translation, etc. These labeled DNA oligonucleotides corresponding to CDRs are particularly useful as probes. After the labeled DNA oligonucleotide probes have hybridized to the bound mRNA, the filters are washed extensively under stringent conditions (see, e.g., Maniatis, supra, pp. 382-89, incorporated herein by reference) and processed for signal development. When the label is radioactive, autoradiography permits identification of those bound fragments of mRNA which do not hybridize with the germline probes and thus produce no autoradiographic signal. These non-hybridizing mRNA fragments represent CDRs in which the germline sequence has been rearranged. The immortalized B cells in which the nucleotide sequence encoding the expressed IgM has been rearranged from germline in only one CDR can be selected using this screening step.

According to an alternate embodiment of this step of the method, the mRNA extracted from the immortalized B cells selected in step (1) is reacted with reverse transcriptase to prepare complementary single stranded DNA (cDNA). The cDNA is separated from the mRNA, digested with one or more restriction enzymes and is then separated into fragments by gel electrophoresis. The fragments are transferred to a solid substrate, such as a nitrocellulose or a nylon filter, usually by blotting and exposed to specific labeled germline DNA sequences obtained from the animal from which the B cells were obtained. The localization on the filter of the cDNA fragments which hybridize with the labeled germline DNA sequences is detected by signal development. When the label is radioactive, the localization on the filter of the hybridizing cDNA fragments is revealed by autoradiography. The cDNA fragment(s) which does(do) not hybridize with the labeled DNA probes represent(s) those in which the sequence of the CDRs have been rearranged from the germline sequence. Those immortalized B cells in which the nucleotide sequence encoding the expressed IgM has been rearranged from germline in only one CDR can be selected using this screening step.

In the practice of this alternative embodiment, the poly-A mRNA is incubated with an oligo-dT primer, reverse transcriptase and the four deoxyribonucleoside triphosphates (dNTPs). The RNA is removed from the RNA/cDNA hybrid thus formed by raising the pH of the reaction mixture. The Southern blot technique is then used to detect the specific rearranged DNA sequences in the single stranded cDNA (see, Southern, 1975, J. Mol. Biol. 98:508) as follows: The cDNA is digested with one or more restriction enzymes, mixed with marker DNA fragments of known length so that their positions can be used to estimate the lengths of the experimental cDNA fragments. The DNA mixture is then separated via gel electrophoresis and transferred by blotting to a nitrocellulose filter. Single stranded DNA corresponding to the germline sequences of the variable region genes of the animal from which the B cells were obtained are radiolabeled and used as probes to determine hybridization with the bound cDNA. Autoradiography permits identification of those bound fragments of cDNA which do not hybridize with the germline probes. These non-hybridizing cDNA fragments represent CDRs in which the germline sequence has been arranged.

According to yet another alternative embodiment of this step of the invention, polyvalent antibodies against germline variable region genes (hereinafter "anti-CDR antibodies") of the animal from which the immortalized B cells selected in step (1) were obtained are prepared using the germline CDR DNA or mRNA sequences or the amino acid sequences encoded by such germline CDRs as an immunogen in an animal different from that from which the B cells were derived. For instance, if the selected B cells were derived from a mouse, then the anti-CDR antibodies can be obtained in a rabbit or a goat. If necessary, the DNA, mRNA or amino acid sequence used an immunogen can be coupled to a carrier and administered with or without an adjuvant. The anti-CDR antibodies are then employed as the capture antibody in an immunoassay such as an ELISA, a dot blot immunoassay, sandwich immunoassays, etc. to screen either the cDNA, mRNA or IgM immunoglobulins obtained from the immortalized B cells selected in step (I). The DNA, mRNA or IgM fragments obtained from the selected cells which do not bind to the anti-DNA, anti mRNA or anti-IgM anti-CDR antibodies represent those CDRs that have been rearranged. The immortalized B cells in which the nucleotide sequence encoding the expressed IgM has been rearragned from germline in only a single CDR can be selected using this screening step.

6.1.3. Determining the Sequence of the Rearranged CDR

According to the third step of the method of the invention, the sequence of the single CDR which has been rearranged from germline and which was identified in step (2) of the method of the invention is determined. When the CDR is identified using either non-hybridizing or non-binding mRNA or cDNA fragments, the non-hybridizing or non-binding mRNA or cDNA is isolated and sequenced using conventional techniques. Using the nucleotide sequence of this single CDR which differs from germline, the amino acid sequence encoded is predicted. Alternatively, the amino acid sequence of the IgM produced by the cells having a nucleotide sequence rearragned from germline in only a single CDR can be determined using conventional amino acid sequencing methods, such as Edman degradation. The amino acid sequence encoded by such single CDR is the desired MRU of the present invention.

The mRNA is sequenced directly by a modified dideoxy-chain termination method as described by Geliebter et al., (1986, proc. Nat'l. Acad. Sci. 83: 3371-75, the disclosure of which is incorporated herein by reference). Briefly, oligonucleotide primers specific for germline variable gene regions of the animal from which the B cells were derived are prepared, radiolabeled and incubated with poly A-mRNA in annealing buffer. The RNA-primer annealing buffer is added to an aliquot of transcription buffer containing reverse transcriptase and one dideoxyribonucleoside triphosphate (ddNTP) (i.e., ddATP, ddCTP, ddGTP or ddTTP). The reaction is stopped and the ethanol precipitate applied to a sequencing gel.

The cDNA is sequenced by known methods such as the dideoxy chain-termination method of Sanger (1977, Proc. Nat'l Acad Sci. USA 74:5463-67) or the Maxan and Gilbert (1977, Proc. Nat'l Acad Sci. USA 74:560-64) method or a combination of these methods. As is known by those of skill in the art, commercially available automated DNA sequencers are particularly useful for rapidly and efficiently determining the nucleotide sequence of even large fragments of DNA. (see, e.g., Knight, 1988, Biotech. 6:1095-96).

If the germline sequences for the animal from which the selected B cells were obtained are known, the sequence of the single CDR can be compared to verify that it differs from such sequence. In practice, the comparison is preferably performed using a computer with an appropriate software package to compare the specific DNA sequence determined with that of germline sequences which are publicly available. Examples of publicly available databases containing germline sequences include, but are not limited to the National Biomedical Research Foundation database and Intelligenetic Package (see, Smith et al., 1986, Nucleic Acids Res. 14:17-20; Dayhoff, ed., 1978, Atlas of Protein Sequence; Kabat et al., eds. 1987, Sequences of Proteins of Immunological Interest, 4th ed., U.S. Dept. of Health and Human Services, 800 pp).

When the CDR is identified using anti-amino acid anti-CDR antibodies, the amino acid sequence of the identified CDR can be directly determined using conventional methods such as Edman degradation, including the use of automated sequenators.

6.1.3.1. Nucleotide Sequences

The invention is intended further to encompass the mRNA and DNA nucleotide sequences of the single CDRs, identified using steps (1)-(3) described above, which encode the peptide and or polypeptide MRUs. These nucleotide sequences are particularly useful to prepare not only the MRUs but also novel polypeptide and protein conjugates of the invention see, Sections 6.1.4 and 6.4, infra).

6.1.4. Synthesizing MRUs

Once the desired M has been identified using steps (1)–(3) above of the present invention, the specific amino acid sequence comprising such peptide or polypeptide can be prepared using any of a number of conventional synthetic methods known to those of skill in the art. For example, the desired MRU can be prepared using any conventional method for chemical synthesis of peptides or polypeptides such as the solid phase method developed by Merrifield et al. (1963, J. Am. Chem. Soc. 85: 2149; 1982, Biochem. 21:5020; reviewed by Barany and Merrifield in Vol. 2 of The Peptides, Gross and Mierinhofer, eds., Academic Press, Inc., New York, pp. 1–284) or the liquid phase method described in Bodanszky, ed., Principles of Peptide Synthesis, Springer-Verlag pp.(1984).

Conventional recombinant DNA techniques can also be used to prepare the MRU. Accordingly, the DNA sequence encoding the desired MRU is inserted into a vector to form a recombinant DNA molecule or virus which is capable of replication in a compatible host cell. As would be appreciated by those of skill in the art, provided the proper replication, transcription and translation signals are correctly arranged on such recombinant DNA molecule, the DNA sequence encoding the desired MRU can be properly expressed in any of a variety of expression vectors including transformed bacterial cells or in permissive eukaryotic cells infected with a recombinant virus or recombinant plasmid carrying a eukaryotic origin of replication. Such well known recombinant techniques are described by Maniatis et al., [Molecular Cloning: A Laboratory Manual, Cold Spring Harbor Symposium, 545 pp. (1982), the disclosure of which is incorporated hereby by reference; Berger and Kimmel, eds., Guide to Molecular Cloning Techniques, Methods in Enzymology Vol. 152, Academic Press, Inc., San Diego, Calif. 812 pp. (1987)].

Once the desired MRU has been prepared, the specific binding of the peptide or polypeptide to the macromolecule or ligand used as Ag is tested, using any of the screening methods enumerated in Section 6.1.1, to insure that the MRU indeed binds specifically to the Ag and mimics the binding specificity of the intended molecular recognition site.

According to yet another alternate embodiment of the present invention, the above-described steps of the present method can be combined and performed using a computer with access to databases comprising the DNA and/or RNA sequences which encode monoclonal antibodies of the IgM isotype or of databases of amino acid sequences of such immunoglobulins. In practice, the publicly available databases are screened to identify those monoclonal antibodies which bind specifically to an Ag containing a molecular recognition site complementary to the desired MRU. Thus, if the desired MRU is intended to mimic the recognition site on a ligand, the databases are screened for IgM immunoglobulins specific for antibodies directed against the ligand and if the desired MRU is intended to mimic the recognition site of a receptor or binding protein, immunoglobulins specific for the ligand are screened. Examples of publicly available databases including antibody sequences include, but are not limited to the National Biomedical Research Foundation database and Intelligenetic Package (see, Smith et al., 1986, Nucleic Acids Res. 14:17–20; Dayhoff, ed., 1978, Atlas of Protein Sequence; Kabat et al., eds. 1987, Sequences of Proteins of Immunological Interest, 4th ed., U.S. Dept. of Health and Human Services, 800 pp). Once a group of IgM's specific for the chosen Ag are selected using this computer-based embodiment of the invention, the DNA sequences encoding such IgM's are compared with that of germline sequences to identify those having a variable region in which only a single CDR differs from that of the germline sequence. Such MRUs are synthesized and screened using any of the above-mentioned screening assays to verify that the thus identified MRU indeed binds specifically to the Ag and mimics the molecular recognition site intended.

The MRUs of the invention also include altered amino acid sequences in which functionally equivalent amino acid residues are substituted for residues within the sequence resulting in a silent change i.e., no adverse effect on the binding specificity of the MRU. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

In addition, as explained in detail, infra, Section 6.4, the MRUs of the present invention are useful as components of conjugates having a first domain which mimics the specificity and binding affinity of a desired molecular recognition site and a second domain which has effector activity. When the second domain is a peptide or a polypeptide moiety, the conjugate can be prepared as a fusion protein or peptide, i.e., the product expressed by parts of two protein encoding genes ligated together so that their reading frames remain in-phase. Such fusion proteins or peptides can be prepared using any of the above-mentioned chemical or recombinant techniques either alone or in combination.

6.2. MRUs with Enhanced Affinity

In certain applications, it may be desirable to prepare MRUs or conjugates of MRUs with enhanced affinity for the Ag recognized by the molecular recognition site which the MRU is designed to mimic. According to one embodiment of this mode of the invention, the MRUs prepared according to the present system can be modified according to the following procedure. Briefly, the DNA sequence encoding the particular MRU, termed "parent MRU", is chemically synthesized. Point mutations are introduced into the DNA sequence by random chemical alterations of the sequence as it is synthesized. Each of the family of mutant DNA sequences thus formed is introduced and cloned in an appropriate expression vector using conventional recobminant DNA techniques. The family of MRUs expressed is screened for binding to Ag, for example, on nitrocellulose filters. The MRU's having higher afinity than the parent MRU are identified using a competitive antigen binding assay versus the parent MRU (see generally, Cambpell, supra, pp. 195-199 for a description of competitive assays)

According to an alternate embodiment of this mode of the invention, conjugates of MRUs with enhanced affinity for the Ag recognized by the molecular recognition site which the MRU is designed to mimic are prepared by attaching multiple copies of the MRU to a macromolecule which has multiple sites for binding the MRUs without substantially interfering with the binding specificity and/or affinity of the MRUs. As a result, such conjugates have enhanced functional affinity for the molecular recognition site in much the same way as multivalent IgM immunoglobulin molecles have higher affinity than IgG immunoglobulin molecules [see Karush, The Immunoglobulins, Litman and Goodman, eds; Plenum Press, New York pp. 85-116 (1978)].

According to yet another alternative embodiment of this mode of the invention, conjugates of MRUs with enhanced affinity for the Ag recognized by the molecular recognition site which the MRU is designed to mimic are prepared by covalently attaching multiple copies of the MRU or fragments thereof in tandem thus forming a polymeric MRU conjugate. Such polymeric MRU conjugates can be prepared by covalently attaching a number of MRUs in tandem either directly or via a linker moiety or alternatively by ligating a number of copies of the nucleotide sequence encoding the MRU in tandem and expressing such sequence as a fusion protein in a compatible host cell. In either case, the tandem array of MRUs forming the conjugate are attached without substantially interfering with the binding specificity of the MRUs.

According to still another alternate embodiment of the invention, MRUs with enhanced affinity for the Ag recognized by the molecular recognition site which the MRU is designed to mimic are prepared by modifying the amino acid sequence of an MRU identified according to the invention as described above, by tandemly attaching a series of amino acid residues comprising a fragment of the MRU thus forming a novel family of MRUs. The family of MRUs is screened for binding to Ag, for example, on nitrocellulose filters. The MRUs having higher afinity than the parent MRU are identified using a competitive antigen binding assay versus the parent MRU (see generally, Cambpell, supra, pp. 195-199 for a description of competitive assays).

6.3. Ags

As indicated supra, Section 6.1.1, an Ag is any molecule or substance which is or contains a molecular recognition site, including molecules and substances which function as receptors for ligands, including but not limited to antibodies, enzymes, binding proteins, etc., and those which function as ligands. According to the present invention, any substance can be used as an Ag so long as it can function at least as a hapten, i.e., a molecule which binds specifically to an antibody although it may not be capable, alone, of causing the production of an antibody. When the Ag selected is a hapten, it must be coupled to a carrier moiety such as, for example, keyhole limpet hemomycanin, bovine serum albumin, ovalbumin, fowl immunoglobulin or any other known carrier etc. before being used in the method of the invention. Any antigen which is capable of inducing an antibody response can be used in the method of the present invention.

The Ag used in the practice of the present invention is chosen according to the purpose of the intended application, i.e., the binding specificity of the molecule which the desired MRU is intended to mimic. Such Ags include, but are not limited to: moieties which are more conventionally termed "antigens" such as bacterial, fungal, viral, mycoplasmal, parasitic, histocompatability or differentiation antigens; hormones; neurotransmitters; peptides that may act as both neurotransmitters and/or systemic hormones; neurohormones; pheromones; biotin; signal substances including signal peptides and proteins; growth factors; enzyme substrates and cofactors; enzyme activators and inhibitors; transition-state analogs for chemical reactions such as those which are facilitated by catalysts; contractile proteins; RNA; DNA; transport proteins; immunoglobulins, enzymes; receptors and receptor proteins; lectins and other binding proteins such as avidin and strepavidin, etc. In addition to moieties more conventionally termed antigens, including such as bacterial, fungal, viral, mycoplasmal, parasitic, histocompatibility or differentiation antigens, Table I presents a non-exhaustive list of ligands which can be used as the Ags according to the method of the present invention. Table II presents a non-exhaustive list of the kinds of macromolecules which can be used as the Ag according to the method of the present invention. In some instances, it is useful to employ an Ag which comprises a combination of more than one category of molecules containing more than one molecular recognition site. In other instances, it may be advantageous to employ an Ag which comprises a complex macromolecule which is composed of subunits which by virtue of their spatial relationships create conformational determinants.

TABLE I
EXAMPLES OF LIGANDS USEFUL AS AGs TO PREPARE MRUs

I. Hormones

| | |
|---|---|
| Oxytocin | Insulin |
| Vasopressin | Glucagon |
| Angiotensin | Adrenocortico- |
| Melanocyte- | tropic hormone |
| stimulating | Thyroid-stimulating |
| hormone | hormone |
| Somatostatin | Follicle-stimulating |
| Thyrotropin- | hormone |
| releasing | Luteinizing |
| hormone | hormone |
| Gonadotropin- | Growth hormone |
| releasing | Prolactin |
| hormone | Corticotropin- |
| Testosterone | releasing |
| Estradiol | hormone |
| Progesterone | Growth hormone- |
| Cortisol | releasing |
| Aldosterone | hormone |
| Vitamin D | Parathyroid |
| Gastrin | hormone |
| Secretin | Calcitonin |
| Somatotropin | Chorionic |
| Prostaglandins | gonadotropin |
| Neurotensin | Chorionic |
| Vasoactive Intestinal | somatomammotropin |
| Peptide | |
| Atrial Natriuretic | |
| Peptide | |
| Thyroxine | |
| Triiodothyronine | |

II. Neurohormones

Enkephalins
Endorphins

III. Neurotransmitters

| | |
|---|---|
| Dopamine | Epinephrine |
| Norepinephirine | Serotonin |
| Glutamate | 7-Amino Butyric Acid |
| Acetylcholine | |

IV. Growth Factors

Epidermal Growth Factor

TABLE I-continued
EXAMPLES OF LIGANDS USEFUL AS AGs TO PREPARE MRUs

Nerve Growth Factor
Platlet-Derived Growth Factor
Angiogenin
Fibroblast Growth Factor
Endothelial Cell Growth Factor
Granulocyte Colony Stimulating Factor
Granulocyte-Macrophage Colony Stimulating Factor
Interleukin 1
Interleukin 2
Interleukin 3
Interleukin 4
Thymopoietin
Erythropoietin
Transforming Growth Factor V. Plant Hormones Absciic acid    Indolacetic acid
Zeatin       Gibberellic acid VI. Pheromones Yeast factor a
Yeast α factor
Insect Pheromones VII. Enzyme-Cofactors and/or Substrates Coenzyme A
Fibrinogen
Angiotensinogen VIII. Effectors of Enzyme Activity Activators
Inhibitors IX. Transition State Analogs for Enzymes Transition-State analogs for hydrolysis of:
Esters
Carbonates
Peptides X. Pharmaceutical Agents Which Bind to Receptors Lovastatin
Cimetidine
Ranitidine
Bromocriptine mesylate
Mecamylamine
Isoproterenol and derivatives thereof

TABLE II
EXAMPLES OF MACROMOLECULES USEFUL AS AGs FOR PREPARING MRUs

I. Immunoglobulins
 Antibodies specific for any "classical" antigens
 Antibodies specific for antibodies against ligands such as those listed in Table I.

II. Receptor/Binding Proteins
 Receptors for ligands such as those listed in Table I
 Cell Receptors for viruses
 T-Cell Receptors
  α/β
  γ/δ
 Sensory Receptors
  Taste
  Smell
 Lectins
  Concanavalin A
  Wheat Germ agglutinin
  Soybean lectins
  Potato lectin
  Lotus seed lectin
 Binding Proteins
  Avidin
  Streptavidin
  Sperm Binding Proteins Such as ZP3
 Egg Binding Proteins III. Enzymes
 Protein enzymes
 RNA enzymes
 Catalytic antibodies As used in Table II, the term "enzyme" is intended to encompass the myriad of macromolecules which are characterized by catalytic activity and specificity and which serve as catalysts of biological and/or biochemical systems. [For a general description of the activity and illustrative examples of the kinds of macromolecule intended, see Stryer, Biochemistry, 3d ed., W. H. Freeman and Co., N.Y., pp. 177–259 (1988); Lehninger, Principles of Biochemistry, Worth Publishers Inc., pp. 207–76 (1982) the disclsoures of which are incorporated herein by reference].

Additionally, when employed according to the method of the invention, the Ag need not be used in purified form. Thus, an Ag which may be found as part of a more complex substance such as a viral particle, a cell surface or cell surface preparation or extract, or even a tissue or organ surface and which can be presented in situ to B cell lymphocytes and still induce an antibody response can be utilized in situ according to the present invention. For example, if the Ag is a bacterial cell surface antigen, it can be used in the method of the invention either in purified form or while attached to fragments or whole bacterial cells.

6.4. Conjugates

The MRUs of the present invention are useful not only alone as agents that mimic the binding specificity of a variety of substances but also as components of conjugates. The conjugates of the present invention comprise a first domain which is an MRU that mimics the binding specificity and binding affinity of a desired molecular recognition site and a second domain that has effector activity. Any molecule or molecular fragment that can be attached to an MRU without destroying either the binding specificity of the MRU or the effector activity of such molecule or molecular fragment can be used as the second domain of a conjugate of the invention. In some instances, the second domain can comprise a second MRU which has effector activity. For example, an MRU which by virtue of its specificity for and binding to a given DNA sequence has a regulatory effect on such DNA sequence can be attached as an effector domain to another MRU which has specificity for a given cell, tissue or organ site. It this case, the first MRU targets the conjugate to the desired site and the second MRU exerts its regulatory activity at the desired site.

The two domains of the conjugates may be attached either directly by any covalent coupling means or via an intermediate linker moiety between the two domains. A linker is intended to include any compatible moiety having at least two reactive groups, one to react with the first binding domain and one to react with the domain having effector activity. Linkers suitable for forming conjugates of the invention include, but are not limited to the branched linkers, cleavable linkers, spacers and cleavable elements, and non-cleavable linkers described in U.S. Pat. No. 4,867,973.

According to an embodiment of this mode of the invention, the linker moiety can also function as an additional "targeting" moiety to further refine the target specificity of the conjugate. In such case, the conjugate comprises three functional domains. As with any linker, one end of the linker moiety, having such additional functional activity, is attached to the binding domain and the other end is attached to the effector domain. For example, when the binding domain is specific for a cell surface receptor or ligand, a linker can be used which also has specific affinity for another sub-cellular region such as the nucleus or a component thereof, the endoplasmic reticulum, the transmembrane portion of the cellular envelope, the mitochondrion, the chloroplast, etc. In this case, the effector domain can be a therapeutic agent, such as a toxin, like ricin, or an antisense composition which acts particularly at a nuclear or other sub-cellular target. Examples of amino acid sequences which can serve as a linker moiety having additional functional activity to direct the conjugate to a sub-cellular site are described in Stryer, L., ed., Biochemistry, 3d. ed., W. H. Freeman and Co., New York, at pp. 767–86; Dunbar et al., 1989, Sci. 245: 1493–96 (KDEL, endoplasmic reticulum), the disclosures of which are incorporated herein by reference. Amino acid sequences including those such as signal sequences of hydrophobic amino acids commonly containing alanine, leucine, valine, isoleucine and phenylanine aid translocation across the endoplasmic reticulum; mitochondrial entry sequences commonly containing positively charged residues such as serine and threonine; chloroplast entry sequences containing positively charged resides such as serine and theonine; nuclear localization sequences such as that of the T antigen of SV40 virus containing five consecutive, positively charged residues, i.e., P-K-K-R-K-V-, etc., can be employed as the linking moiety according to this mode of the invention. Those of skill in the art will readily understand that the fusion proteins or peptides of this embodiment can be prepared using any of the chemical or recombinant techniques mentioned in Section 6.1.3 either alone or in combination.

When used as a component of a conjugate, the MRU targets the conjugate to the molecular recognition site for which it is specific and the effector domain exerts its activity at the target site. In those instances when the molecular recognition site for which the MRU is specific is a transition state analog for a catalytic enzyme, the MRU will have not only binding specificity, but also catalytic activity at the target site. Effector activities are intended to include biological, pharmacological and enzymic activities as well as support.

As mentioned above in Section 6 2, the effector domain can be a multivalent macromolecule with multiple sites for attachment of the MRUs such that the conjugate has enhanced affinity for the molecular recognition site for which the MRU is specific. Polymeric conjugates of MRUs are also encompased by the MRU conjugates of the invention (see supra, Section 6.2).

Moieties which can be used as a second or effector domain of a conjugate of the invention depend upon the application for which the conjugate is intended. In some instances, the conjugate is intended for use in vivo either for a diagnostic or therapeutic purpose. In such case, the effector moiety must possess sufficient aqueous solubility so that when coupled, either directly or via a linker moiety, to an MRU, the resulting conjugate possesses sufficient aqueous solubility so that it is suitable for in vivo use. On the other hand, when the conjugate is intended for uses which do not involve administration to a human or an animal, the conjugates encompass those which are either soluble or insoluble in aqueous solutions.

When the conjugate is intended for diagnostic purposes, the MRU domain affords the ability to target the conjugate to a desired site and the effector domain provides a "reporter" moiety which allows the conjugate to be detected at the desired site. Any category of reporter moiety can be used to prepare the diagnostic conjugates of the invention including such as radioactive isotopes including radioactive metal ions, radioopaque dyes, fluorogenic compounds, chemiluminescent compounds, non-radioactive paramagnetic compounds detectable using nuclear magnetic resonance spectroscopy, positron-emitting agents which can be detected using positron emission tomography, dyes detectable using conventional spectroscopy, etc. As will be readily appreciated by those of skill in the art, the diagnostic conjugates which can be employed in either in vivo or in vitro applications encompass both aqueous soluble and aqueous insoluble compositions.

When the conjugate is intended for therapeutic purposes, the MRU domain affords the ability to target the conjugate to a desired site and the effector domain provides a biologically or pharmaceutically active moiety which enables the conjugate to effect its therapeutic activity at the desired site. A large number of biologically active moieties can be used as effector domain of the the therapeutic conjugates of the invention including, for example, pharmaceutical agents such as analgesics, antibacterial agents, antifungal agents, antineoplastic and other antiproliferative agents, antiparasitic agents, antimycoplasmic agents, antiviral agents, antiinflammatory agents, antidepressants, anticoagulants, antithrombolytic agents, agents which alter membrane permeability, etc., and biologically active agents such as hormones, neurotransmitters, neurohormones, DNA, toxins and active fragments of toxins, enzymes, cytokines, lymphokines, growth factors, tumor necrosis factor, interferons, and active fragments of such biologically active agents, etc. As will be readily appreciated by those of skill in the art, the therapeutic conjugates which can be employed in either in vivo or in vitro applications encompass both aqueous soluble and aqueous insoluble compositions.

According to another embodiment of the invention, conjugates of MRUs useful for diagnostic or therapeutic purposes comprise an MRU domain which affords the ability to target the conjugate to a desired site and an effector domain which has affinity for or the ability to bind a metal ion. The metal ions which bind to the effector domain can be radioactive metals such as alpha-, beta- or gamma-emitting ions, positron-emitting ions, or non-radioactive paramagnetic ions or fluorescent ions, etc. A specific example of such an effector domain is the carboxy terminal end of the amino acid sequence of metallothionein, i.e., KCTCCA, which serves as a means of binding metal ions, including zinc, cadmium, lead, copper, silver, mercury, bismuth, cobalt, nickel, technetium and rhenium. Other metal-binding peptides useful as an effector domain according to this embodiment include, but are not limited to, other cysteine-containing peptides in metallothionein such as the following: S C T C T S S C A, A C K A C K C, G C S K C A Q G C V, C K G A A D K C T C C A, and homologues of these in which serine residues are replaced by threonine, glycine, or alanine. Still other examples of metal binding peptide sequences include histidine-rich peptides (see Morgan et al., 1989, J. Mol. Recog. 2: 122) including, but not limited to, the heme binding sequence G H F P F H W and homologues thereof. This sequence is especially useful for chelation to copper as well as other metal ions. Yet another example of a useful metal binding peptide sequence is found in the zinc finger motif (see Lee et al., 1989, Science 245: 635), having amino acid sequence Y K C G L C E R S F V E K S A L S R H Q R V K K N and homologues. This peptide is expected to bind metal ions including zinc, cadmium, lead, copper, silver, mercury, bismuth, cobalt, nickel, technitium, and rhenium.

When the conjugate is intended for chemical and/or catalytic purposes, the conjugates can be classified into several different types. In one type of conjugate for these purposes, the MRU domain provides the molecular recognition and/or catalytic activity and the effector domain provides a support or matrix for the MRU domain. A large number of solid or matrix supports can be employed to prepare conjugates for these purposes. Suitable supports include, but are not limited to latex spheres, agarose beads, dextran beads, activated glass beads, polystyrene, polypropylene, rubbers, polyesters, polyamides, polymers of methacrylates, polymers of vinylchloride such as polyvinylchloride, cellulose, silica gels, and derivatives thereof, etc.

In another type of conjugate for chemical and/or catalytic purposes, the MRU domain provides the molecular recognition and/or catalytic activity and the effector domain provides a support function such that the conjugate is sufficiently soluble so that it is useful catalytically in solutions.

In yet another type of the conjugate for chemical and/or catalytic purposes, the MRU domain provides the recognition and/or catalytic activity and the effector domain provides catalytic activity which may be the same or different from the catalytic activity provided by the MRU domain. In this instance, the effector domain is an enzyme or active fragment thereof which catalyzes any of a variety of chemical reactions and the conjugate can be used catalytically in solution.

6.5. Applications for MRUs and Conjugates of MRUs

MRUs are particularly useful in systems in which the following factors are important: molecular recognition and a high degree of binding specificity; low molecular weight and potential lower immunogenicity when administered in vivo; more rapid clearance from blood and more rapid diffusion into target organs, tissues and/or cells when administered in vivo; ability to combine with an additional effector function; ability to produce higher valent conjugates with consequent enhanced functional affinity; cost-effectiveness; etc. Thus, according to the present invention, MRUs and conjugates of MRUs are used in a wide variety of applications, including, but not limited to uses in the fields of biomedicine; biological control and pest regulation; agriculture; cosmetics, environmental control and waste management; chemistry; catalysis; nutrition and food industries; military uses; climate control; etc. The applications briefly described below are intended as illustrative examples of the uses of the MRUs and conjugates of MRUs and are in no way intended as a limitation thereon. Other applications will be readily apparent to those of skill in the art and are intended to be encompassed by this application.

The MRUs and conjugates containing MRUs of the invention are used for a wide variety of in vitro and in vivo applications in the fields of biomedicine and bioregulation or control. In these applications, the MRUs and conjugates of MRUs are employed for example, as mimetic replacements for compositions such as antibodies or immunoglobulins and fragments thereof, hormone-receptors, receptors for neurotransmitters, receptors for signal substances or proteins, and enzymes as well as mimetic replacements for antigens or immunogens, hormones, signal substances, neurotransmitters and agonists or antagonists of endogenous brain receptors for substances such as alcohol, psychoactive drugs, growth factors, pheromones, effectors of enyzme activity, gene regulatory proteins, regulators of localized cell division, etc.

Depending upon the purpose, the MRUs and conjugates the invention can be administered in vivo to animals, including humans, by a number of routes, including such as injection (e.g. intravenous, intraperitoneal, intramuscular, subcutaneous, intraauricular, intramammary, intraurethrally, etc.) topical application (e.g. on afflicted areas), and by absorption through epithelial or mucocutaneous linings (e.g. ocular epithelia, oral mucosa, rectal and vaginal epithelial linings, respiratory tract linings, nasopharyngeal mucosa, intestinal mucosa, etc.). Delivery to plants, insects and protists for bioregulation and/or control can be achieved by direct application to the organism, dispersion in the organism's habitat, addition to the surrounding environment or surrounding water, etc.

The MRUs and conjugates of the invention can also be employed for in vitro diagnostic and therapeutic applications by administration to cells in vitro (e.g., animal, including human cells, plant cells, protists, etc.)

In the nutrition and food industries, the MRUs and conjugates containing MRUs can be employed as mimetic replacements for any of the ligands which are recognized and specifically bound by sensory receptors which function as taste or olfactory sensors. For instance, ligands such as those which interact with receptors that mediate the taste for sweetness can be mimicked by the peptide or polypeptide MRUs of the invention. (See, Schiffman et al., The Receptors, Vol. IV, Conn, ed; Academic Press, N.Y. pp. 315-77). Such MRUs could thus serve as mimetic replacements for these ligands for sweet taste.

In the chemical industry, the MRUs and conjugates of the invention which can mimic the binding specificty of immunoglobulins, enzymes, binding proteins, or ligands for such macromolecules can be employed in a larger variety of separations, purifications and preparative methods.

In the field of catalysis, MRUs can be designed to mimic antibodies specific for transition state analogs of enzymes which catalyze any of a variety of chemical reactions.

Alternatively, MRUs can be designed to mimic the binding specificity of the active site of an enzyme, or an effector of an enzyme such as an enzyme inhibitor or an activator of an enzyme. Such MRUs can be employed to catalyze or regulate the catalysis of a variety of enzyme reactions which are useful in industrial applications.

In addition, as explained in greater detail in Section 6.4, supra, a number of different types of conjugates of MRUs can be employed as catalytic agents for reactions which are carried out either on solid supports or in solutions.

In the field of waste management, MRUs and conjugates of the invention can be employed in separations, purifications and degrative processes.

In the field of military uses and biological control, MRUs can be employed as mimetic replacements for and as novel immunogens in vaccines, as antigens in assays for toxic pathogens and toxins, as anti-toxins or antidotes, as radioprotectants, etc.

In the field of climate control, MRUs and conjugates of the invention can be employed as scavengers of pollutants which interfere with or destroy the ozone layer; as mimetics for ligands that serve as cloud seeders to increase precipitation, etc.

Finally, as indicated above, the above described applications are merely illustrative examples of the myriad uses intended for the MRUs and conjugates of the invention. Enumeration of such illustrative examples is in no way intended as a limitation either on the MRUs or the uses of the MRUs of the invention. As will be readily appreciated by those of skill in the art, the method of the present invention provides a novel way to prepare novel MRUs, which mimic the molecular recognition site of any molecule so long as it can function as a hapten or an antigen. Methods for using any such MRUs are clearly within the scope of this invention.

The following examples are presented for purposes of illustration and are not intended to limit the scope of the invention in any way.

7. EXAMPLE: PREPARATION OF AN MRU

The following experiment illustrates the preparation of an MRU that mimics the binding specificty of an antibody that reacts with a mucin antigen associated with human adenocarcinoma according to one embodiment of the invention.

The mucin antigen is obtained in purified form from samples of human breast or colon carcinoma using a monoclonal antibody (IgG1) specifically reactive with said antigen and obtained from hybridoma cell line ACTTC No. HB8108 (hereinafter "B72.3 antibody") described in U.S. Pat. No. 4,522,918 issued to Schlom et al. (see, Nuti et al., 1982, Int.. J. Cancer 29:539-45). Alternatively, the mucin antigen can be used in the form of a cell surface membrane extract obtained from samples of human breast or colon carcinoma. In either case, according to an in vivo mode of the invention, the mucin antigen is administered via an intraperitoneal route to experimental Balb/c mice for 2-3 days. On day 3, the animals are sacrificed, the spleens aseptically removed and spleen cells are immortalized using conventional fusion techniques developed by Kohler and Milstein (see review by these authors, 1980, Sci. Amer. 243:66-74).

The immortalized hybridoma cells are plated at low density, i.e., about 60% growth proportion and allowed to proliferate in in vitro cell culture for about 10-14 days in HAT medium.

The immortalized hybridoma cells obtained at about 10-14 days in cell culture are screened to identify those which have binding specificity for the mucin antigen and to identify those which express immunoglobulin of the IgM class using ELISA assays.

An aliquot of the immortalized cells identified above which express IgM immunoglobulin specific for the mucin antigen is then cultured in vitro in RPM1 1640/10% fetal calf serum and cells are harvested. Total RNA is isolated from the harvested cells after centrifrugation through a CsCl cushion and poly-A-mRNA isolated using an oligo-dT cellulose column as described by Auria et al. (1972, Proc. Natl. Acad. Sci. 69:264-68).

The mRNA is then dot blotted into nitrocellulose filters which are then blocked to prevent non-specific binding when labeled germline specific single-stranded obligonucleotide probes are subsequently applied to the filters. Single stranded oligonucleotide DNA probes are prepared using the known germline sequences of murine variable region genes (see, e.g. Kabat et al., supra) and end labeled using radioactive P-32 (see, Maniatis, supra, pp. 109-124). The filters are then extensively washed under stringent conditions (see Maniatis, supra, p. 388). The washed filters are exposed to autoradiographic film to permit identification of those portions of bound mRNA which do not hybridize with the specific, radiolabeled germline DNA probes. Where no autoradiographic signal is detected, non-hybridizing mRNA fragments representing CDRs in which the germline sequence has been rearranged have been identified. Those immortalized cell lines in which the sequence encoding the expressed IgM is rearranged in only one CDR are selected using this mode of the invention.

The nucleotide sequence of the single CDR sequence identified above is determined as follows. The mRNA encoding the selected CDR is sequenced directly as described in Geliebter et al. (1986, Proc. Nat'l. Acad. Sci. 83: 3371-75).

The putative amino acid sequence encoded by the nucleotide sequence of the single CDR determined above is predicted using the conventional information of the genetic code and the amino acid sequence comprising desired MRU is chemically synthesized using the solid phase synthetic method of Merrifield (1963, J. Am. Chem. Soc. 85:2149).

The specific binding ability of the prepared MRU is verified using a competitive ELISA assay in which the mucin antigen is used as the antigen and the MRU competes with the antibody produced by immuno-selected B cells.

8. EXAMPLE: A FAMILY OF CONJUGATES USEFUL FOR IMAGING THROMBI

The following example presents a novel family of conjugates of MRUs which are fusion peptides that are advantageously used for imaging thrombi in vivo. Additionally, it is anticipated that these conjugates will also be useful for localization at other sites of activated platelets, including such as sites of localized inflammation, sites of infection, particularly abcesses, and sites of tumors with clots.

8.1. Conjugates of MRUs: Anti-Thrombic Fusion Peptides

The CDR3 region of PAC-1 monoclonal antibody described by Taub et al. (1989, J. Biol. Chem. 264(1): 259-65) constitutes a potential MRU as defined according to the present invention. Using the amino acid sequence of the CDR3 region of PAC-1 antibody as a starting point, a novel family of conjugates of MRUs, which are synthetic fusion peptides, was prepared in accord with the present invention. The conjugates comprise: an MRU domain which is the amino acid sequence encoded by CDR3 of the PAC-1 antibody or a portion thereof, preferably engineered to have enhanced affinity, compared with the MRU obtained from the native CDR3, for activated platelet fibrinogen receptor and an effector domain which is the carboxyl terminal end of the amino acid sequence of metallothionein, i.e., KCTCCA. The effector domain, KCTCCA, quantitatively binds metal ions including such as zinc, cadmium, lead, copper, silver, mercury, bismuth, cobalt, nickel, technetium, rhenium, etc., and thus can serve as a means of attaching a diagnostic or therapeutic metal ion. Examples of such metal ions include but are not limited to radioactive metal ions such as Tc-99m for diagnostic purposes, Re-188, Cu-64 and Cu-67 for both diagnostic and therapeutic purposes, and Bi-212 and Pb-212 for therapeutic purposes. In these cases, the effector domain would serve as either a "reporter" moiety to allow the conjugate to be detected at the target site, or be used to deliver a thereapeutic dose of radioactivity to the appropriate site. Note that some of the above-mentioned radioisotopes, notably Re-188, Cu-67 and Cu-64, could be used for both diagnosis and therapy.

The fusion peptides described here were all synthesized chemically using an automated peptide synthesizer using standard techniques (see generally, Bodanszky, 1984, "Principles of Peptide Synthesis, Springer-Verlag, Berlin).

TABLE III

| PEPTIDE SEQUENCES |
| --- |
| ARRSP SYYRY DGAGP YYAMD YKCTC CA |
| ARRSP SYYRG DGAGP YYAMD YKCTC CA |
| ARRSP SYYRY YDGAG PYYAM DYKCT CCA |
| KCTCC ARRSP SYYRY DGAGP YYAMD Y |
| KCTCC ARRSP SYYRG DGAGP YYAMD Y |
| SPSYY RYDGA GPY KCTCCA |
| SPSYY RGDGA GPY KCTCCA |
| KCTCC APSYY RGDGA PSYYR GDA |
| PSYYR GDYGAP SYYRG DGAPS YYRGD AKCT CCA |
| CKRAR GDDMD DYCKC TCCA |
| SGAYG SRGDG KCTCC A |
| SGAYG SRGDG KCTCC A |
| SGAYG SRGD KCTCC A |
| SYGRG DVRGD FKCTC CA |
| SYRGDSKKC TCCA |
| SYSRG DVGRG DVRGD FKCTC CA |

Table III illustrates the amino acid sequences, ranging from about 8 amino acids to about 39 amino acids, of a family of conjugates of MRUs prepared according to the present invention. The amino terminus of the fusion peptide can be either unblocked or blocked with a group such as acetyl and the carboxy terminus of the fusion peptide can be either unblocked or blocked with a group such as an amide group.

8.2. Activity of the Fusion Peptides

8.2.1. PLASMA STABILITY OF FUSION PEPTIDES

Proteolytic degradation

A representative peptide designated "Pac-2" of the sequence: ARRSPSYYRGDAGPYYAMDYKCCT-CCA was labeled with 125-Iodine via standard techniques (Iodobead) (see Markwell, 1982, Anal. Biochem. 125: 427-32). Stability of the labeled peptide, having either an unblocked or blocked amino terminal end, to proteolytic enzymes in plasma was assayed as follows: Labeled peptides were incubated in fresh citrated human platelet-poor plasma in sealed tubes at 37° C. Aliguots were removed at various times and assayed using reverse phase HPLC. Degradation was calculated by loss of the original radioactive peak on a reverse phase HPLC C-6 column using 0–60% acetonitrile in 20 mM Na phosphate, pH, 6.0. Inhibitors of proteolytic enzymes in plasma were used to identify responsible enzyme classes and included: EDTA (metalloenzymes), benzamidine (serine endoproteases), bestatin (aminopeptidases) and leupeptin (acid proteases). Results are presented in Table IV.

TABLE IV

| IN VITRO PLASMA STABILITY OF A PEPTIDE | | |
| --- | --- | --- |
| Peptide | Inhibitor(s) | Half-Life (min) |
| PAC-2 | — | 2.1 |
| PAC-2 | 1 mM Bestatin | 8.5 |
| PAC-2 | 1 mM Bestatin 1 mM leupeptin 10 mM benzamidine 10 mM EDTA | >120 |
| succ-PAC-2 | — | 17.5 |

As indicated in Table IV, the half-life of PAC-2 in plasma was 2.1 minutes. Inclusion of bestatin, an inhibitor known to block aminopeptidases, increased the half-life to 8.5 minutes. A mixture of 4 proteolytic enzyme inhibitors increased the plasma half-life to greater than 120 minutes. It is also apparent, as shown in Table IV, that blockage of the amino terminus, in this case by a succinimic acid group, also greatly lengthened the half-life in plasma.

Release of technetium from fusion-peptides in plasma

MRU conjugates having a binding domain selected from the peptide sequences shown in Table III and an effector domain having the amino acid sequence KCCTA were radiolabeled with Tc-99m using a commercially available labeling kit (Glucoscan, DuPont, Billercia, Mass.) as follows:

Up to 1.25 ml (50 mCi) of pertechnetate (Syncor Inc.) was removed by syringe without exposure to air into a Glucoscan (60 ug stannous chloride, 200 mg glucoheptanoate under nitrogen) vial. The desired amount was transferred into 50 ug of peptide in Low Dissolved Oxygen saline. The amount of peptide has been varied to achieve specific activities as high as 2 mCi/ug. Theoretical maximum loading is 330 mCi/ug for a 1600 Dalton peptide.

Reduction of pertechnetate (Tc-VII) to the chelatable form with oxidation state (Tc-V) was checked by paper chromatography using Whatman-50 developed in acetone. In this system, pertechnetate moves to the solvent front, and all other species of technetium stay at the origin. The percent trans-chelation of Tc-V from glucoheptonate (Glucosan) to peptide was analyzed by silica Instant Thin Layer Chromatography (ITLC) developed with 0.1M saline, pH 6.0. In this system, the peptides remain at the origin, while glucoheptonate-TcO moves to the solvent front.

Tc-99m labeled peptides were incubated in citrated human plasma at 32° C. and 2 ul aliquots were examined periodically for bound and free technetium by ITLC up to 24 hours. In all cases carboxy terminals were blocked with amide groups and in some cases amino terminals were also blocked with acetyl groups to eliminate the issue of proteolysis from these studies. Results are illustrated in FIG. 1.

As shown in FIG. 1, 20–40% of the radioactivity was released from the fusion peptides in the first few hours, followed by relative stability. Incubation with the four protease inhibition mixture for 24 hours produced results identical to those obtained without the inhibitors (data not shown).

The fusion peptides were evaluated for stability of the Tc-99m label by incubating them in neutral buffer, i.e., PBS, pH 7.0, for various times at room temperature. Specifically, 50 μg of peptides Pac-2 and a peptide designated "Pac-19" of the sequence SGAYSRGDGKCT-CCA-a were labeled with 1 mCi of Tc-99m, and incubated in PBS. Aliquots were taken at 2, 4, and 24 hours and evaluated on an Instant Thin Layer Chromatography (ITLC) system developed with 0.1M saline. In this system, peptide-associated Tc-99m remains at the origin while any other form moves to the solvent front. At every time point, the Tc-99m remained at the origin, indicating that the label is stable under these conditions of neutral buffer at room temperature.

In summary, these results indicate that the Tc-99m labeled fusion peptides are stable in neutral buffer for days and did not lose more than about 40% of radiolabel in 24 hours, citrated human plasma at 37° C.

8.2.2. Inhibition of Platelet Aggregation and Binding of Platlets to PAC-1 Antibody The ability of the fusion peptides and of peptides comprising the binding domain of the fusion peptides to inhibit platelet aggregation was assessed as follows:

Platelet poor, human plasma was prepared by centrifugation of citrated human plasma at 900 rpm, Sorvall Rc-3, for 20 minutes at room temperature. 0.5 mL of the platelet solution was placed in the cuvette of a Payton Aggregometer, followed by 50 μL of a solution containing various concentrations, up to 200 μM, of the peptide being assayed. After 1 minute, 5 μL of 10 mM ADP in water was added. The aggregation rate was assessed by a change in the slope of the absorbance curve. Ability of an RGDS tetrapeptide to inhibit platelet aggregation was also included for comparison. Results are tabulated in Table V.

TABLE V

PEPTIDE ACTIVITY ASSAYS

| Peptide[a,b] | IC-50 (μM) Binding | Aggregometer |
|---|---|---|
| RGDS | 50 | 60 |
| ARRSPSYYRGDAGPYYAMDY | 10 | 20 |
| ARRSPSYYRYDAGPYYAMDY | 90 | 21 |
| RGDS | | 40 |
| SYRGDSK-a | | 34 |
| ac-RGDVY-a | | 49 |
| ac-RGDVRGDVY-a | | 7.4 |
| ac-RGDVRGDVRGDVY-a | | 6.8 |
| ac-PSYYRGDGA-a | | 31 |
| ac-PSYYRGDGAPSYYRGDGA-a | | 8.0 |
| SGAYGSRGDGKCTCCA-a | | 48 |
| ac-SGAYGSRGDGKCTCCA-a | | 82 |
| ac-SYGRGDVRGDFKCTCCA-a | | 12 |
| ARRSPSYYRYYDGAGPYYAMDY | n.d. | >500 |
| ac-PSYYRGDGAPSYYRGD-GAPSYYRGDA-a | | 5.7 |
| ac-KCTCCAPSYYRGDGAPS-YYRGDGAPSYYRGDA-a | | 3.5 |
| ac-PSYYRGDGAPSYYRGDGA-PSYYRGDAKCTCCA-a | | 3.5 |

[a]-amide blocked on carboxy terminus
[b]ac-acetyl blocked on amino terminus

The ability of the fusion peptides and of peptides comprising the binding domain of the peptides, specific for the activated platelet fibrinogen receptor, to inhibit the binding of PAC-1 antibody was assessed as follows:

Platelets were isolated by placing 7 ml of platelet-rich-plasma onto a 50 ml column of Sepharose 2-B equilibrated in Walshes 1% BSA buffer (1.0 g NaCl, 0.2 g KCl, 0.2 g MgCl₂, 0.45 g NaH 0.9 g HEPES, 1.0 g BSA and 1.0 g dextrose in sufficient water to make exactly 1 liter), pH 7.45. The cloudiest tubes were pooled to obtain 14 ml of platelets (approximately 300,000/μl). The peptide in Walshes 1% BSA buffer and 20,000 CpM of 125-I-pAC 1 (5 μCi/μg) was added to one ml of this in a microfuge tube. Platelets were next activated with 0.1 μM phorbol myristate acetate or 10 μM ADP at 37 degrees C. After 1 hr, platelets were pelleted at top speed in a horizontal microfuge, washed gently, and the tube bottom removed with dog nail clippers and it, supernatant and wash were counted in a gamma camera. Peptide concentrations were calculated from absorbance at 280 nm, using as extinction coefficient 1400M$^{-1}$ for each tyrosine, except for RGDS, which was weighed. Varied levels of peptide were examined and IC-50 was determined from a graph of % inhibition versus peptide concentration. Results are shown in Table V.

As demonstrated in Table V, the fusion peptides of the invention containing an MRU attached to a KCTCCA sequence and peptides comprising a binding domain of the fusion peptides are active at inhibiting platelet aggregation and/or the binding of the PAC-1 antibody. Surprisingly, the peptides having significantly enhanced binding to activated platelets contain repeats of fragments of the MRU containing an RGD sequence. For instance, peptides containing a single RGD sequence have an IC 50 of about 49 μM; peptides containing—RGDVRGDV—of about 7.4 μM, and peptides having—RGDVRGVRGDV—of about 6.8 μM. It is noted that such enhanced binding with the peptides having a repeat RGD sequence cannot be cross-linking more than one receptor because such peptides are too small. Thus, the enhanced binding seen with such peptides is surprising and could not have been predicted. Moreover, replacement of the RYD or RGD sequence of the binding domain of the fusion peptides with RYYD lead to complete loss of binding activity.

8.3. Use of Fusion Peptides for in vivo Imaging

Two major problems have been encountered in the clinical application of radiolabeled antibodies and antibody fragments for in vivo imaging of thrombi. Firstly, thrombi must be detected in a matter of hours for the data to be of use for the physician. This requires rapid background clearnace which is not easily obtained when whole antibodies or antibody fragments are employed for delivery of the label for imaging. Secondly, in some cases, antibodies and antibody fragments elicit troublesome antibody responses in patients.

The following experiments demonstrate that conjugates of MRUs of the invention, designed to target to thrombi, are rapidly cleared from the circulation and are quickly delivered to the site of a thrombus. It is anticipated that these small fusion peptide conjugates will be less immunogenic and thus less prone to elicit undesirable antibody responses. Thus, it is expected that these conjugates which comprise fusion peptides will be advantageously used for in vivo imaging of thrombi.

Two kg or larger white New Zealand rabbits were anesthetised and a thrombus induced in the jugular vein as follows: the jugular vein was surgically exposed, side branches tied off and a segment of about 1 inch in length was clamped off. A silk thread was introduced through the segment with both ends external. Ten units of bovine thrombin in Tris-buffered saline (TBS) pH 7.5 were added by syringe. After 10 minutes, the clamp was removed and the wound closed. After 1 hour, approximately 50 μg of a MRU conjugate which is a fusion peptide labeled with Tc-99m as described in Section 8.1, supra, was injected via the contralateral ear vein. I-125 labeled fibrinogen was subsequently injected as a control in order to assess normal blood clearance and clot localization. Blood samples were periodically taken in order to determine blood clearance of the fusion peptide and the animals were imaged using a gamma camera over a 4-hour period. The animals were then sacrificed and the amount of Tc-99m and I-125 in various organs was assessed. A Tc-99m labeled nonspecific peptide analogue containing the RYYD sequence served as a control. Results obtained are shown in Table VI and FIGS. 2 and 3.

Figure 2:
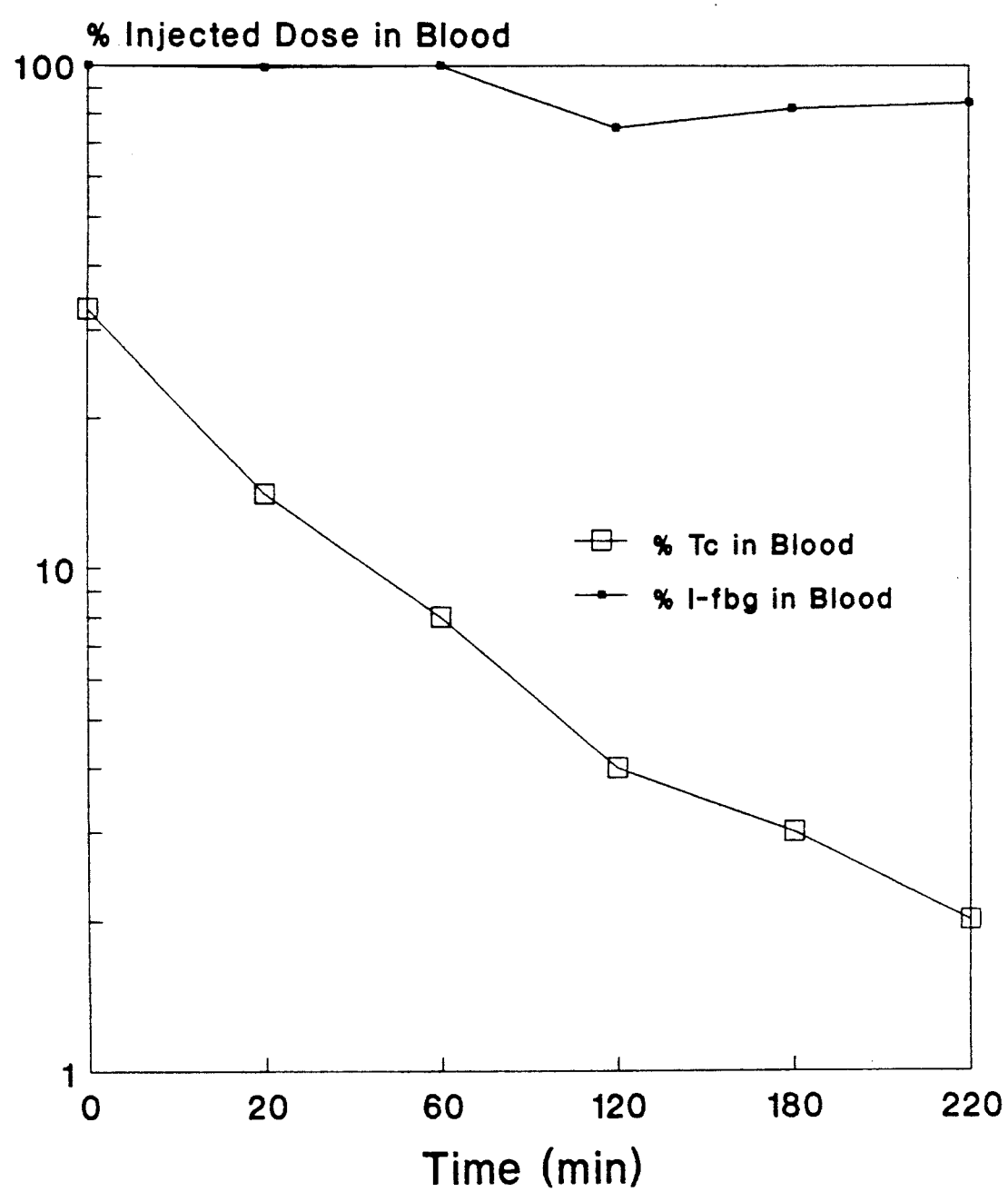

As illustrated in FIG. 2, blood clearance of the Tc-99m labelled peptide was rapid, having a T ½ of about 5 minutes or so. Only about 1-2% of the injected dose remained in the blood circulation at the time of sacrifice, i.e., about 4 hours post-injection. Excretion of Tc-99m took place through the kidneys (data not shown).

Additionally, fractionation of the blood samples into: red blood cell, platelet-white cell and plasma fractions suggested that 1-5% of the radioactivity is in the red cell fraction, 1-2% in the platelet-white cell fraction and the remainder in the plasma. Similar results were obtained when the Tc-99m labeled peptide was incubated with blood drawn from an animal or a human. These results indicate that the Tc-99m-labeled fusion peptides, advantageously, do not bind red blood cells.

TABLE VI

RABBIT THROMBUS MODEL BIODISTRIBUTION AND IMAGING

| RABBIT NO. | PEPTIDE[a] | CLOT WT (MG) | CLOT % ID PER GRAM | CLOT: BLOOD RATIO | IMAGE QUALITY |
|---|---|---|---|---|---|
| 10 | PAC 2 | 65 | 0.010 | 0.84 | POOR |
| 11 | PAC-2 | 52 | 0.011 | 0.92 | POOR |
| 12 | PAC-3 | 14 | 0.031 | 2.48 | NONE |
| 13 | PAC-3 | 44 | 0.019 | 0.92 | NONE |
| 14 | PAC19-A | 77 | 0.028 | 1.09 | GOOD |
| 15 | PAC 19-A | 12 | 0.022 | 1.77 | GOOD |
| 17 | PAC-2 | 133 | 0.008 | 0.57 | FAIR |
| 18 | PAC-2 | 34 | 0.034 | 0.78 | FAIR |
| 19 | PAC-19-C | 42 | 0.029 | 1.57 | GOOD |
| 20 | PAC-2 | 39 | 0.005 | 0.79 | FAIR |
| 24 | PAC-8 | 50 | 0.016 | 1.18 | GOOD |
| 25 | PAC-8 | 58 | 0.020 | 1.37 | GOOD |
| 32 | PAC-16 | 61 | 0.035 | 1.04 | GOOD |
| 33 | PAC-15 | 8 | 0.074 | 2.48 | GOOD |
| 34 | PAC-15 | 31 | 0.016 | 0.81 | GOOD |

Peptide sequences are as follows, where "ac" represents an acetylated amino terminus and "a" represents an amidated carboxy terminus: PAC-2, ac-ARRSPSYYRGDAGPYYAMDYKCTCCA-a; PAC-3, ac-ARRSPSYYRYYDAGPYYAMDYKCTCCA-a; PAC-19-A, SGAYSRGDGKCTCCA-a; PAC-19-C, ac-SGAYSRGDGKCTCCA-a; PAC-8, ac-SYGRGDVRGDFKCTCCA-a; PAC-16, ac-PSYYRGDGAPSYYRGDGAPSYYRGDAKCTCCA-a; PAC-15, ac-KCTCCAPSYYRGDGAPSYYRGDA-a.

Representative biodistribution data obtained after dissection of the rabbits are shown in the Table VI. Note that the moderate levels obtained with these 99m-Tc labeled peptides are still able to give images in the gamma camera. This can be explained by noting (data not shown) that the clots are labeled only on the periphery, while the biodistribution data are obtained by weighing the entire clot.

Figure 3A:
Figure 3B:
Figure 5A:
FIG. 5 (A-D) illustrates images of a rabbit having a thrombus in the left jugular vein after injection of a Tc-99m labeled fusion peptide, designated "Pac-15," of the sequence: ac-KCTCCAPSYYRGDGAPSYYRG-DGAPSYYRGDA-a (see text Section 8.3 for details).
Figure 5B:
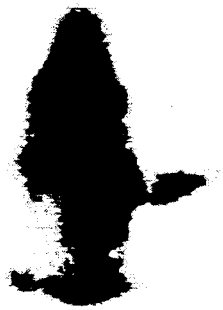
Figure 5C:
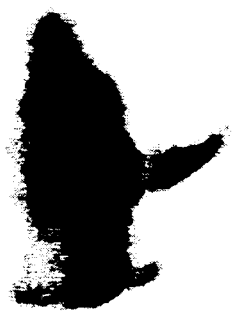
Figure 5D:
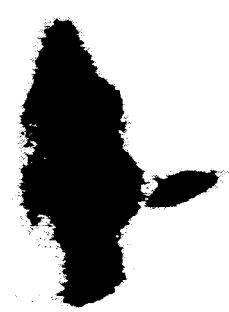
Figure 6A:
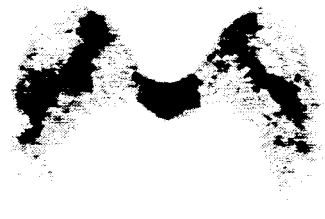
FIG. 6 (A-D) illustrates images of an experimental animal (dog) having a clot in the right femoral vein injected with a Tc-99m labeled peptide designated "Pac-8," a fusion peptide of the sequence: ac-SYGRGDVRGDFKCTCCA-a. Images were taken at 12 minutes, 1, 3 and 4 hours after injection (see text Section 8.3 for details).
Figure 6B:
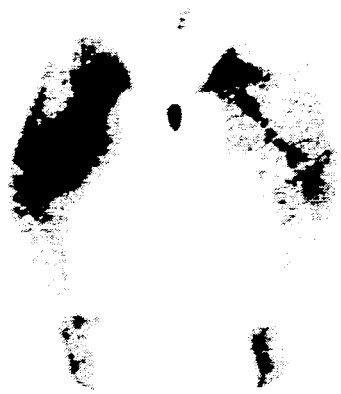
Figure 6C:
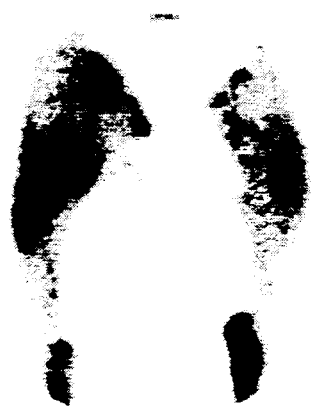
Figure 6D:
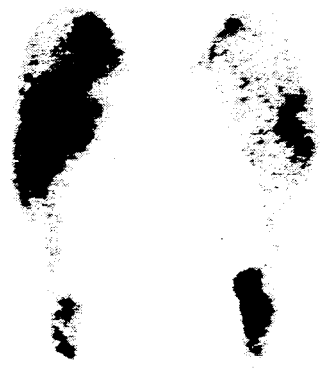
Figure 7:
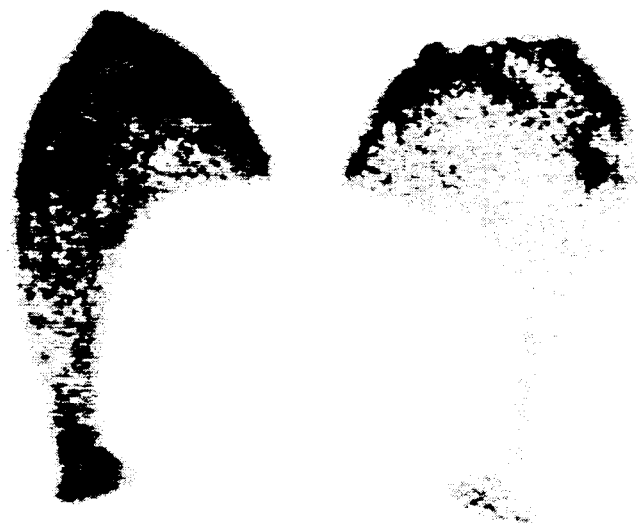
FIG. 7 illustrates an image of an experimental animal (dog) having a clot in the right femoral vein injected with Tc-99m labeled Glucoscan with no peptide (control) (see text Section 8.3 for details).

Representative gamma camera images obtained are presented in FIGS. 3-5. In FIG. 3 (A and B), images obtained in two different animals which received an irrelevant Pac-3 peptide containing the RYYD sequence are shown. These are negative controls. As demonstrated in FIG. 3 (A B), there was no uptake in the region of the clot. This substantiates the lack of platelet inhibition seen with this peptide (Table V). In FIG. 3 (C and D), images obtained in animals which received Pac-8 peptide, specific for activated platelets. FIG. 3C shows the uptake at various time points, and finally after the rabbit had been sacrificed and the thrombus removed. It is clear that the labeled peptide localizes to and images the clot in this model. FIG. 3D is a similar experiment with a second rabbit. Again, it is apparent that the peptide images the clot quickly within about 18 minutes. The image clearly persists to the 4-hour time point.

In order to evaluate the effect of Glucoscan on the localization, one sample of peptide was labeled and then separated using a Baker spe reverse-phase column. The image obtained with this purified peptide was identical to those shown in FIG. 3.

As demonstrated in Table VI and illustrated in FIG. 3, images were focally positive within 1 to 2 hours after injection of the radiolabeled fusion peptides specific to activated platelets. Some images could be visualized in as little as 15-18 minutes. Recruitment of fibrinogen is occurring during the 1-2 hour period (data not shown). Thus, these peptides are advantageously useful for in vivo imaging of thrombi.

FIG. 4 (A-E) and FIG. 5 (A-D) illustrate images obtained in other experimental rabbits which received, respectively, a fusion peptide designated "PAC-16" of the sequence: ac-PSYYRGDGAPSYYRGDGAPSYYRGDAKCTCCA-a and a fusion peptide designated "Pac-15" of the sequence: ac-KCTCCAPSYYRGDGAPSYYRGDGASYYRGDA-a. As shown in these figures, MRU conjugates in which the effector domain was either on the amino terminus or on the carboxy terminus of the binding domain specific for activated platelets clearly localize and permit imaging of the clot. Moreover, these fusion peptides demonstrate the advantageous utility of peptides containing a repeat sequence which is a portion of the "parent" MRU, i.e., PSYYRGDGA is repeated in each of these peptides.

In another series of experiments, a dog model of venous thrombi was used in which a clot was induced in the femoral vein of a dog by means of an embolytic coil. This model is useful to evaluate day-old thrombi. In this study, about 100 μg of a fusion peptide designated "Pac-8" of the amino acid sequence ac-SYGRGDVRGDFKCTCCA-a was labeled with 19 mCi of Tc-99m. Ten mCi of the labeled peptide was injected into a dog having a clot in the right femoral vein. Another animal having a clot in the right femoral vein which received only the Tc-99m Glucosan (used in labeling the fusion peptide) served as the control. Images obtained are shown in FIGS. 4 and 5, respectively for the experimental animal and the control animal.

The images shown in FIGS. 4 and 5 were obtained with a gamma camera placed above the prone dog which was lying on its back. As demonstrated in FIG. 4, there is clear localization into the clot as early as 12 minutes post-injection of the labeled peptide. This localization persisted for more than 4 hours. In addition, both the clot and the endothelial lining of the vein are visualized. This suggests that the peptide reacted with and was able to permit visualization of clots forming along the course of the injured endothelium. This further indicates that the binding activity of these fusion peptides is advantageously useful for localizing clots in vivo. As demonstrated in FIG. 5, when no radiolabeled peptide was added and when only Tc-99m labeled Glucoscan was injected, no localization to the clot was visible even after 4 hours post-injection. This result further substantiates the specificity of the clot visualization seen with the fusion peptides of the invention.

What is claimed is:

1. A compound, comprising a first amino acid sequence having binding activity and affinity for an activated platelet fibrinogen receptor and selected from the group consisting of:
   SYGRGDVRGDF,
   SGAYSRGDG,
   SGAYGSRGDG,
   SYRGDSK,
   PSYYRGDGAPSYYRGDGA,
   PSYYRGDGAPSYYRGDGAPSYYRGDA,
   ARRSPSYYRGDAGPYYAMDY,
attached directly to a second amino acid sequence capable of binding a metal ion selected from the group consisting of:
   KCTCCA,
   SCTCTSSCA,
   ACKACKC,
   GCSKCAQGCV,
   CKGAADKCTCCA,
   GHFPFHW,
   YKCGLCERSFVEKSALSRHQRVKKN,
and such peptides in which either or both the amino or carboxy terminus is blocked.

2. The compound of claim 1, in which the carboxy terminus is blocked.

3. The compound of claim 1, in which the amino terminus is blocked.

4. The compound according to claim 1, in which the amino terminus and the carboxy terminus are blocked.

5. The compound according to claim 1, in which the first amino acid sequence is SYGRGDVRGDF or the peptide thereof in which either or both the amino and carboxy terminus is blocked.

6. The compound according to claim 1, in which the second sequence is a peptide of the sequence: KCTCCA or the peptide in which either or both the amino or carboxy terminus is blocked.

7. The compound according to claim 1, further comprising a metal ion bound to the second amino acid sequence.

8. The compound according to claim 7, in which the metal ion is a radioactive metal ion, a positron-emitting metal ion, a fluorescent metal ion, a chemiluminescent metal ion or a non-radioactive paramagnetic metal ion.

9. The compound according to claim 8, in which the radioactive metal ion is selected from the group consisting of radioactive iostopes of zinc, cadmium, lead, copper, silver, mercury, bismuth, cobalt, nickel, technetium and rhenium.

10. The compound according to claim 1, in which the first amino acid sequence is SYGRGDVRGDF and the second amino acid is sequence KCTCCA or the peptide in which the amino or carboxy terminus is blocked.

11. The compound according to claim 10, in which the carboxy terminus is amidated and the amino terminus is acetylated.

12. The compound according to claim 10, further comprising a metal ion bound to the second amino acid sequence.

13. A peptide selected from the group consisting of:
   SYGRGDVRGDFKCTCCA,
   KCTCCAPSYYRGDGAPSYYRGDGAPSYYRGDA, and
   PSYYRGDGAPSYYRGDAPSYYRGDAKCTCCA
and such peptides in which either or both the amino or carboxy terminus is blocked.

14. The peptide according to claim 13, further comprising a metal ion bound to the KCTCCA group.

15. The compound according to claim 13, in which the metal ion is a radioactive metal ion, a positron-emitting metal ion, a fluorescent metal ion, a chemiluminescent metal ion or a non-radioactive paramagnetic metal ion.

16. The compound according to claim 15, in which the radioactive metal ion is selected from the group consisting of radioactive isotopes of zinc, cadmium, lead, copper, silver, mercury, bismuth, cobalt, nickel, technetium and rhenium.

* * * * *